United States Patent
Lih et al.

(10) Patent No.: US 9,404,891 B2
(45) Date of Patent: Aug. 2, 2016

(54) APPARATUS FOR AND METHOD OF MONITORING CONDENSED WATER IN STEAM PIPES AT HIGH TEMPERATURE

(71) Applicants: Shyh-Shiuh Lih, La Canada Flintridge, CA (US); Hyeong Jae Lee, South Pasadena, CA (US); Yoseph Bar-Cohen, Seal Beach, CA (US); Xiaoqi Bao, San Gabriel, CA (US)

(72) Inventors: Shyh-Shiuh Lih, La Canada Flintridge, CA (US); Hyeong Jae Lee, South Pasadena, CA (US); Yoseph Bar-Cohen, Seal Beach, CA (US); Xiaoqi Bao, San Gabriel, CA (US)

(73) Assignee: CALIFORNIA INSTITUTE OF TECHNOLOGY, Pasadena, CA (US)

( * ) Notice: Subject to any disclaimer, the term of this patent is extended or adjusted under 35 U.S.C. 154(b) by 324 days.

(21) Appl. No.: 14/109,470

(22) Filed: Dec. 17, 2013

(65) Prior Publication Data

US 2014/0107954 A1   Apr. 17, 2014

Related U.S. Application Data

(63) Continuation-in-part of application No. 13/043,499, filed on Mar. 9, 2011, now Pat. No. 8,632,244.

(60) Provisional application No. 61/312,164, filed on Mar. 9, 2010.

(51) Int. Cl.
| | |
|---|---|
| *G01N 29/024* | (2006.01) |
| *G01F 23/296* | (2006.01) |
| *G01N 29/44* | (2006.01) |
| *G01N 29/50* | (2006.01) |

(52) U.S. Cl.
CPC .......... *G01N 29/024* (2013.01); *G01F 23/2962* (2013.01); *G01N 29/4472* (2013.01); *G01N 29/50* (2013.01); *G01N 2291/02836* (2013.01); *G01N 2291/044* (2013.01); *G01N 2291/101* (2013.01)

(58) Field of Classification Search
CPC . G01N 29/4472; G01N 29/50; G01N 29/024; G01N 2291/02836; G01N 2291/044; G01N 2291/101; G01F 23/2962
USPC ............................................... 73/649; 702/54
See application file for complete search history.

(56) References Cited

U.S. PATENT DOCUMENTS

| | | | | |
|---|---|---|---|---|
| 4,570,489 A | * | 2/1986 | Baumaire | ............. F22B 37/421 376/252 |
| 5,625,150 A | * | 4/1997 | Greene | ................... G01N 29/14 376/249 |
| 8,632,244 B2 | * | 1/2014 | Bar-Cohen | .......... G01F 23/2962 374/117 |
| 8,800,373 B2 | * | 8/2014 | Kleven | ...................... F16T 1/48 73/46 |

* cited by examiner

*Primary Examiner* — J M Saint Surin
(74) *Attorney, Agent, or Firm* — Milstein Zhang & Wu LLC; Joseph B. Milstein

(57) ABSTRACT

A system and method for monitoring the properties of a fluid, such as water, in a steam pipe without mechanically penetrating the wall of the pipe. The system uses a piezoelectric transducer to launch an ultrasonic probe signal into the pipe. Reflected ultrasonic signals are captured in a transducer, which can be the same transducer that launched the probe signal. The reflected signals are subjected to data processing, which can include filtering, amplification, analog-to-digital conversion and autocorrelation analysis. A result is extracted which is indicative of a property of the fluid, such as a height of the condensed fluid, a cavitation of the condensed fluid, and a surface perturbation of the condensed fluid. The result can be recorded, displayed, and/or transmitted to another location. One embodiment of the system has been constructed and tested based on a general purpose programmable computer using instructions recorded in machine-readable non-volatile memory.

20 Claims, 36 Drawing Sheets

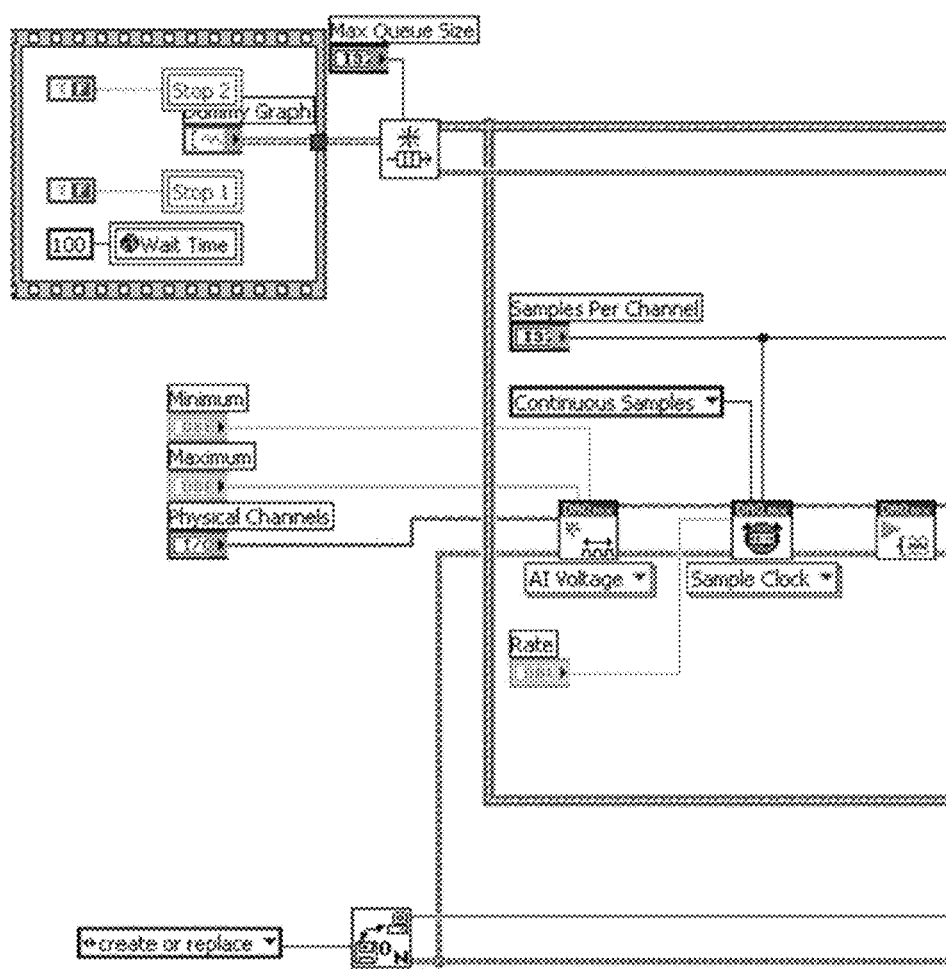
FIG. 6A
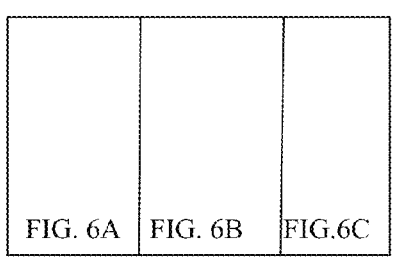

Reflection from the
top plate pulse

- Reflection signal from the coupon
- Ringing between plates shows the condition of no bonding.

Reflection signals from the bonded coupon shows no ringing between the plates.

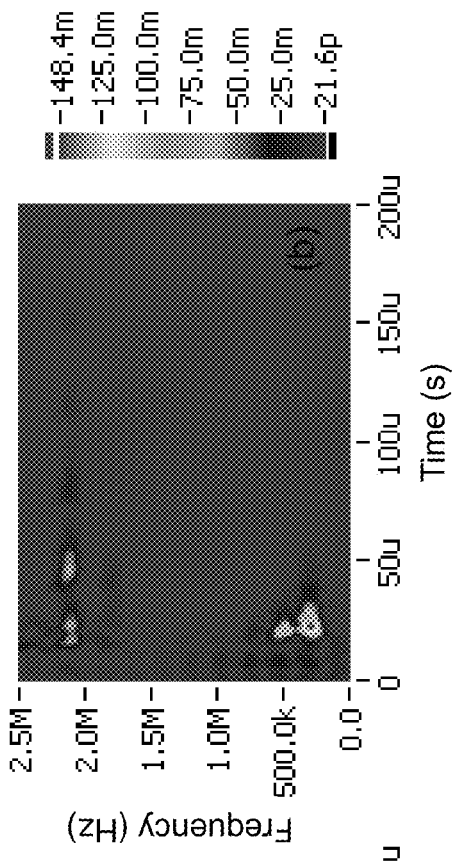
FIG. 25A
FIG. 25B
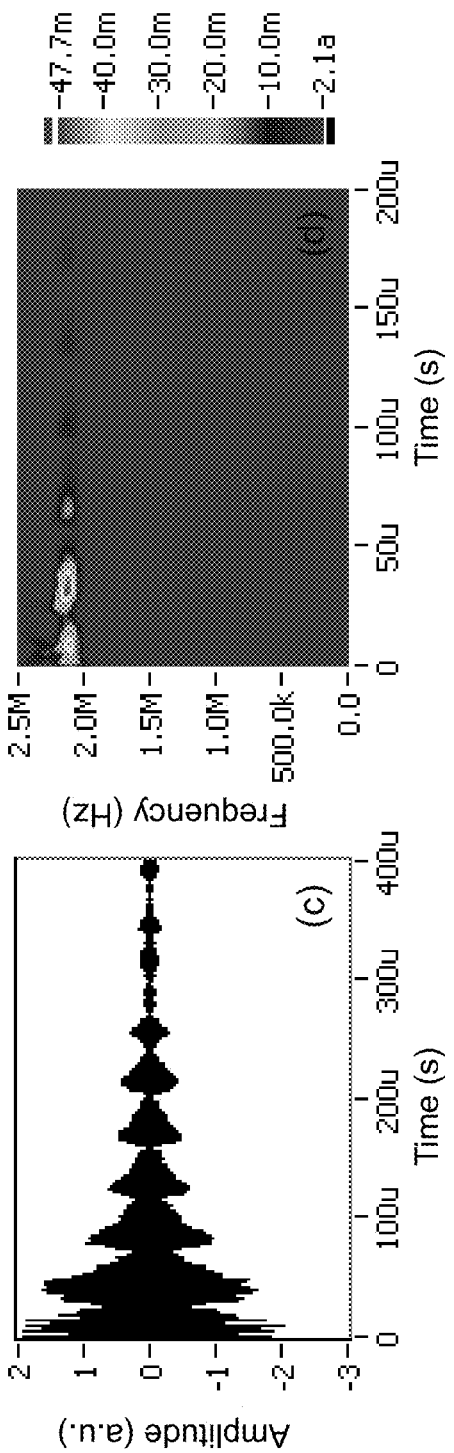
FIG. 25C
FIG. 25D

APPARATUS FOR AND METHOD OF MONITORING CONDENSED WATER IN STEAM PIPES AT HIGH TEMPERATURE

CROSS-REFERENCE TO RELATED APPLICATIONS

This application is a continuation-in-part of co-pending U.S. patent application Ser. No. 13/043,499 filed Mar. 9, 2011, which application claimed priority to and the benefit of then U.S. provisional patent application Ser. No. 61/312,164 filed Mar. 9, 2010, each of which applications is incorporated herein by reference in its entirety.

STATEMENT REGARDING FEDERALLY FUNDED RESEARCH OR DEVELOPMENT

The invention described herein was made in the performance of work under a NASA contract, and is subject to the provisions of Public Law 96-517 (35 USC 202) in which the Contractor has elected to retain title.

FIELD OF THE INVENTION

The invention relates to systems and methods for measuring the contents of piping systems in general and particularly to systems and methods that operate at high temperature and high pressure.

BACKGROUND OF THE INVENTION

Generally, steam pipes are used as part of a district heating system many cities carrying steam from central power stations under the streets to heat, cool, or supply power to high rise buildings and businesses. Some businesses and facilities also use the delivered steam for cleaning and sterilization. In addition to providing space and water heating, the steam is used in numerous restaurants for food preparation, laundries and dry cleaners, as well as to power absorption chiller systems for air conditioning. The New York Steam Company began providing this service in lower Manhattan in 1882. Today, Con Edison operates this system that has grown to become the largest commercial steam system in the world. Con Edison now transmits about 14 million tons per year of steam through its pipe system. The steam flows at a relatively high speed and it can reach over 100 miles per hour. It is common to see the emission of vapors from manholes in Manhattan and it mostly caused by external water being boiled resulting from contact with a steam pipe and it does not necessarily represent a leak in the steam system.

One of the concerns to such a system is the excitation of water hammer that may lead to serious consequences including damaged vents, traps, regulators and piping. The water hammer is caused by accumulation of condensed water that is trapped in a portion of horizontal steam pipes. The velocity of the steam flowing over the condensed water causes ripples in the water creating buildup of turbulence and resulting in the water formation of a solid mass or slug that fills the pipe. The slug of the condensed water can travel at the speed of the steam striking the first elbow that is encountered in its path. The force can be comparable to a hammer blow and can be sufficiently large to break the back surface of the elbow.

There is a need for systems and methods that can provide real time monitoring of pipes that operate at high temperature and elevated pressure.

SUMMARY OF THE INVENTION

According to one aspect, the invention features a monitoring system for determining the status of a steam pipe. The monitoring system comprises a programmable computer which when operating under control of a set of instructions recorded on a machine readable memory performs the steps of: controlling the emission of a probe ultrasonic signal having a frequency in the range of 2.25 Mega Hertz and above from an ultrasonic signal generator into a steam pipe; receiving from an ultrasonic signal receiver an electrical signal representative of an ultrasonic response signal which is generated in the steam pipe in response to the probe ultrasonic signal; processing the electrical signal by application of one or more of a filter, a moving average, a window, a transformation, a Shannon Energy Envelope and an autocorrelation method to produce a result representing a status of the steam pipe; and performing at least one of recording the result, displaying the result, and transmitting the result to another system.

In one embodiment, the filter is selected from the group consisting of a low pass filet, a high pass filter and a band limit filter.

In another embodiment, the window is a predetermined searching window.

In yet another embodiment, the transformation is selected from the group consisting of a time to frequency domain transformation, Fourier Transform, a Hilbert Transform, and a Hilbert-Huang Transformation.

In still another embodiment, the ultrasonic signal generator and the ultrasonic signal receiver are the same ultrasonic device.

In a further embodiment, the programmable computer which when operating under control of a set of instructions recorded on a machine readable memory performs the additional step of converting the electrical signal from an analog signal to a digital signal.

In yet a further embodiment, the result representing a status of the steam pipe includes information about liquid water in the stem pipe.

In an additional embodiment, the information about liquid water in the steam pipe is indicative of a depth of the liquid water.

In one more embodiment, the information about liquid water in the steam pipe is indicative of at least one of a turbulent flow, of bubble generation, of cavitation, of a shock and of a vibration in the liquid water.

In still a further embodiment, the programmable computer is a general purpose programmable computer.

According to another aspect, the invention relates to a machine-readable medium having recorded thereon a set of instructions which when operating on a programmable computer causes the programmable computer to perform the steps of: controlling the emission of a probe ultrasonic signal having a frequency in the range of 2.25 Mega Hertz and above from an ultrasonic signal generator into a steam pipe; receiving from an ultrasonic signal receiver an electrical signal representative of an ultrasonic response signal which is generated in the steam pipe in response to the probe ultrasonic signal; processing the electrical signal by application of one or more of a filter, a moving average, a window, a transformation, a Shannon Energy Envelope and an autocorrelation method to produce a result representing a status of the steam pipe; and performing at least one of recording the result, displaying the result, and transmitting the result to another system.

In one embodiment, the filter is selected from the group consisting of a low pass filet, a high pass filter and a band limit filter.

In another embodiment, the window is a predetermined searching window.

In yet another embodiment, the transformation is selected from the group consisting of a time to frequency domain transformation, Fourier Transform, a Hilbert Transform, and a Hilbert-Huang Transformation.

In still another embodiment, the ultrasonic signal generator and the ultrasonic signal receiver are the same ultrasonic device.

In a further embodiment, the programmable computer is caused to perform the additional step of converting the electrical signal from an analog signal to a digital signal.

In yet a further embodiment, the result representing a status of the steam pipe includes information about liquid water in the stem pipe.

In an additional embodiment, the information about liquid water in the steam pipe is indicative of a depth of the liquid water.

In one more embodiment, the information about liquid water in the steam pipe is indicative of at least one of a turbulent flow, of bubble generation, of cavitation, of a shock and of a vibration in the liquid water.

In still a further embodiment, the programmable computer is a general purpose programmable computer.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 6A, FIG. 6B and FIG. 6C, collectively referred to as FIG. 6, is a diagram illustrating the process flow associated with the Labview® code that was developed for the automation of the data acquisition and processing. A diagram illustrating the relationship of FIG. 6A, FIG. 6B and FIG. 6C appears on the sheet containing FIG. 6A.

FIG. 25A is a graph showing the received signal as a function of time.

FIG. 25B is a graph showing the received signal after being subjected to a high-pass filter as a function of time.

FIG. 25C is a plot of the time-frequency spectrum of the received signal of FIG. 25A using the short-time Fourier transform (STFT).

FIG. 25D is a plot of the time-frequency spectrum of the filtered signal of FIG. 25C using the short-time Fourier transform (STFT).

DETAILED DESCRIPTION

Herein disclosed is a steam pipe health monitoring system that operates in-service to track at high temperatures through a wall in real-time the height of condensed water. The system accounts for the effects of water flow and cavitation. For this purpose, ultrasonic waves were used to perform data acquisition of reflected signals in pulse-echo and via autocorrelation the data was processed to determine the water height. Transmitting and receiving the waves is done by a high temperature piezoelectric transducer that has a high Curie temperature above the expected temperature range.

It is believed that the novel features of this disclosure include:

A system that monitors the height of water condensation in steam pipes through the wall of the pipe.

A water condensation height measurement system that performs in conditions of height disturbances and in the presence of cavitations and bubbles.

A monitoring system that operates at high temperature conditions in the field.

The Problem

The problem that was addressed is the need for a monitoring system that provides assurance against potential accidents and system failures in aging steam pipe systems in many cities. An effective in-service health monitoring system is needed to track water condensation in real-time through the wall of the steam pipes. The system is required to measure the height of the condensed water from outside the pipe while operating at temperatures that are as high as 250° C. The system needs to account for the effects of water flow and cavitation. In addition, it is desired that the system does not require perforating the pipes, so as to avoid reducing the structural integrity of the piping system. In addition, a sensor operates through a perforation in a pipe poses an operational problem when the sensor fails and needs to be replaced, because the system needs to be shut down to change the sensor.

The Solution

The disclosed system uses ultrasonic waves in pulse-echo and it acquires reflected signal data. Using autocorrelation it determines the water height while eliminating the effect of noise and multiple reflections from the wall of the pipe. The feasibility of the disclosed invention was demonstrated in the lab.

Figure 1:
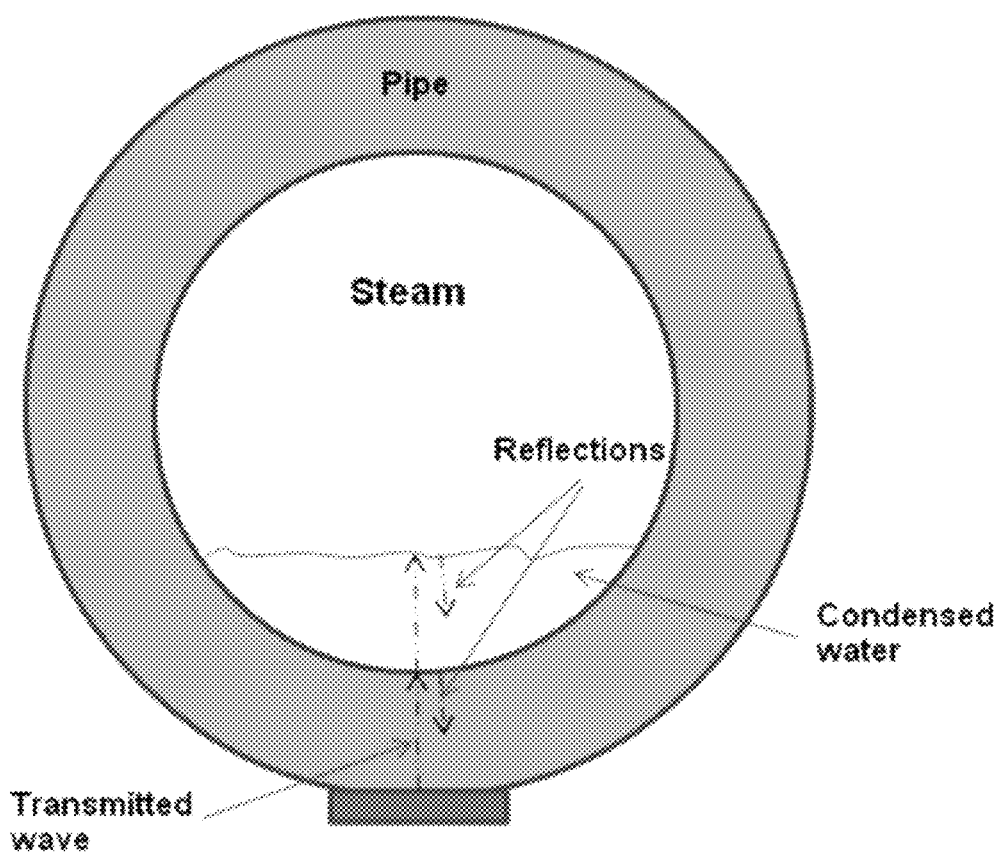
FIG. 1 is an illustration of the condensed water level monitoring using time-of-flight measurements of reflected ultrasonic waves.

The disclosed system performs a nondestructive monitoring through the wall of steam pipes and automatically measures the height of condensed water while operating at the high temperature conditions of 250° C. For this purpose, the ultrasonic pulse-echo method is used where the time-of-flight of the wave reflections inside the water are measured and is multiplied by the wave velocity to determine the height. The pulse-echo test comprises the steps of emitting ultrasonic wave pulses from a piezoelectric transducer and receiving the reflections from the top and bottom of the condensed water (see FIG. 1). As shown in FIG. 1, a single transducer is used as transmitter as well as the receiver of the ultrasonic waves. To obtain high resolution a broadband transducer is used and the frequency can be in the range of 2.25 to 10 MHz providing sharp pulses in the time domain allowing for higher resolution in identifying the individual reflections.

The pulse-echo transducer is connected to either the transmitter (or function generator), which sends high voltage signals to generate the elastic wave, and to the receiver, which amplifies the attenuated reflected waves that are converted to electric signals. To avoid damage to the receiver, the large signal from the generator is blocked by an electronic switching mechanism from reaching the receiving circuitry. To assure the operation of the transducer at the specific application temperature range, the piezoelectric transmitter/receiver is selected with a Curie temperature that is much higher than the operating temperature of the system to be measured. As examples, the electromechanical properties of lithium niobate (LiNbO$_3$) crystals and Bismuth Titanate (Bi$_4$Ti$_3$O$_{12}$) with high Curie temperature are given in Table 1. In addition the system can be improved by introducing a heat sink between the transducer and the steam pipe reducing in this way the temperature requirements on the transducer.

Figure 2:
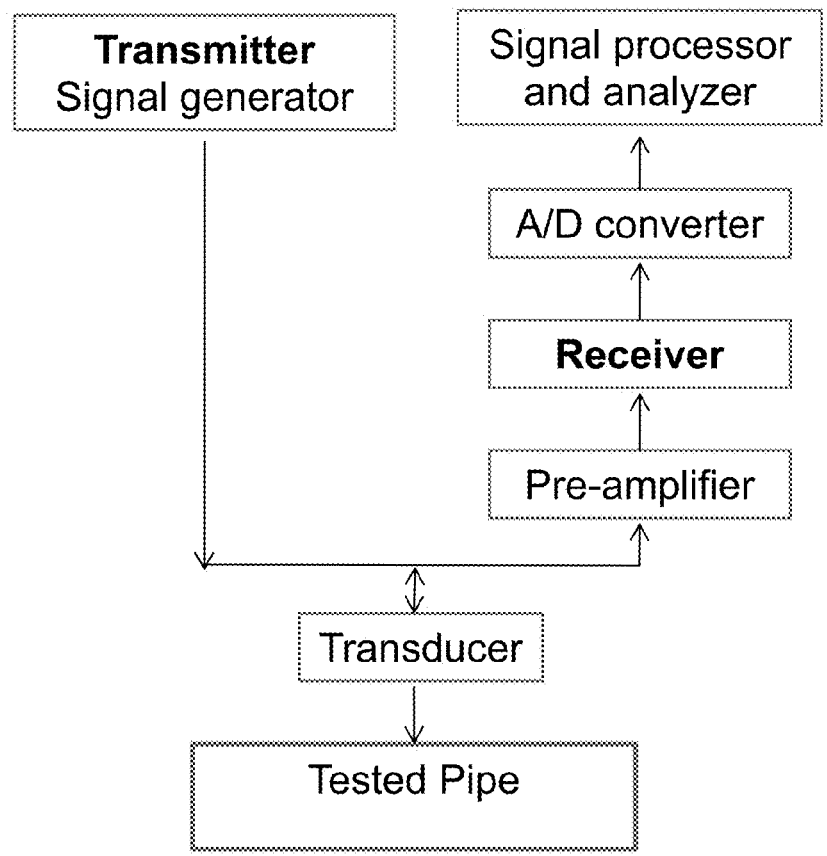
FIG. 2 is a schematic diagram of the test system.

The test system that was used in the demonstration of the feasibility of our invention has the block diagram configuration that is shown in FIG. 2. A pipe that represents the steam system was produced as part of the test-bed and it consists of a steel pipe made of A53B steel alloy having a 16 inch diameter and ⅜ inch wall thickness. Plumbing for water entry to fill the pipe and for draining were made and the side walls were produced of Plexiglas for viewing the inside and to measure the water height. Various transducers with different diameters and transmission frequencies were mounted from the bottom of the pipe in a pulse-echo configuration and were driven by a transmitter/receiver and were aligned for maximum reflections using a miniature manipulator.

Figure 3:
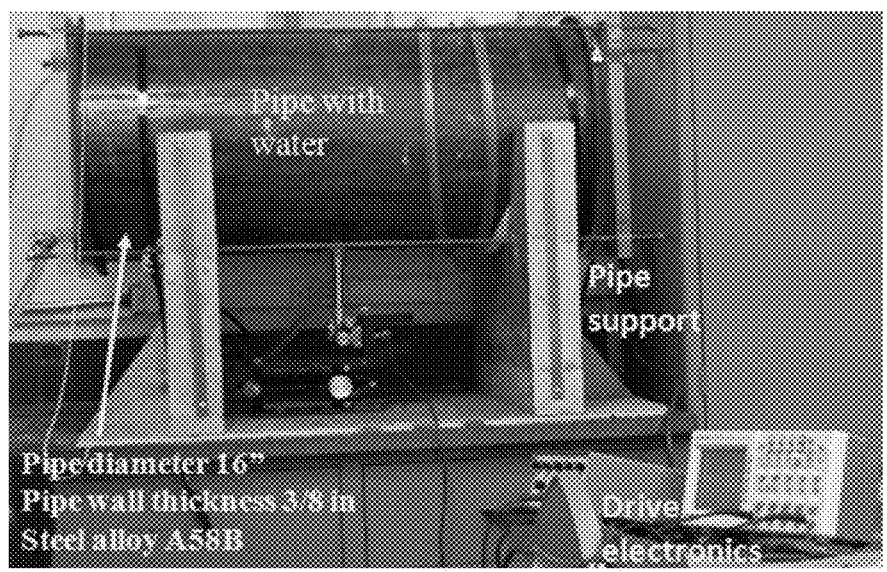
FIG. 3 is an image of the test-bed simulating the steam pipe and the in-situ ultrasonic test setup.
Figure 4A:
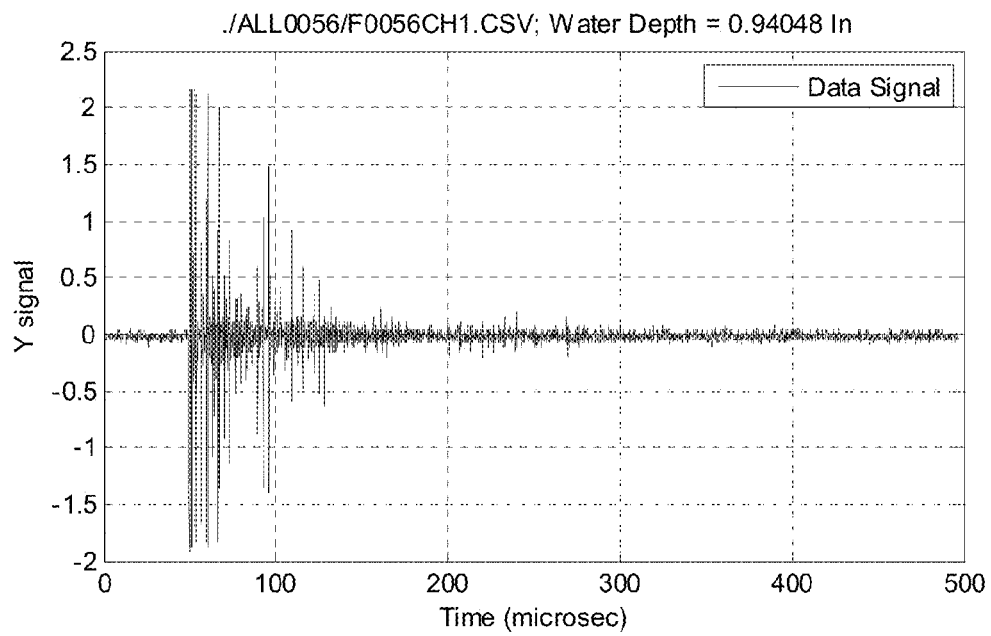
FIG. 4A is a graph illustrating the reflections patterns received from the pipe with 1.0 inch water height.
Figure 4B:
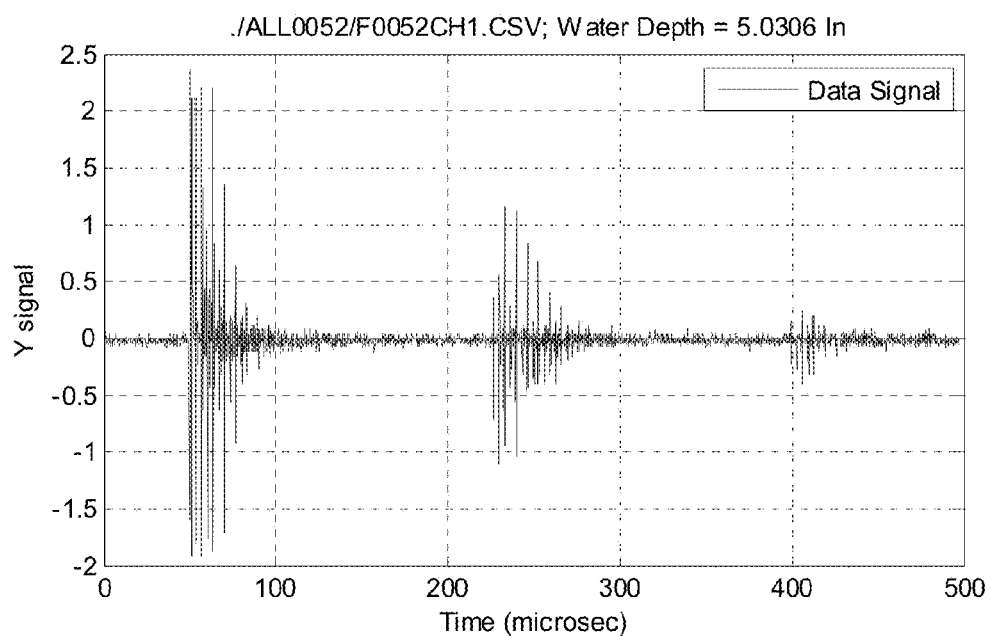
FIG. 4B is a graph illustrating the reflections patterns received from the pipe with 5.0 inch water height.

A photograph of the test-bed is shown in FIG. 3. The results have proven the feasibility of providing high sensitivity, resolution and accuracy of the measurements. An example of the measured reflections pattern from the pipe with 1.0 inch water height is shown in FIG. 4A. FIG. 4B shows data for a water height of 5 inches. As can be seen, a significant number of reflections occur in the pipe wall (the first set of reflections) and it is compounded by reflections from the top surface of the water (the second set of reflections). This large number of reflections makes it difficult to base the determination of the height on simple time-of-flight data and therefore an autocorrelation technique was used.

from the side wall of the tank. This can partially explain the reason for the relatively large error in the case of the smaller height of the water.

TABLE 2

The difference between the measured and the autocorrelation calculation of the water height.

| Water height (inch) | Calculated height (inch) | Difference % |
|---|---|---|
| 1.0 | 0.94 | 6.0 |
| 2.0 | 1.96 | 4.0 |
| 3.0 | 2.89 | 3.7 |
| 4.0 | 4.13 | 3.3 |
| 5.0 | 5.03 | 0.6 |

Figure 6B:
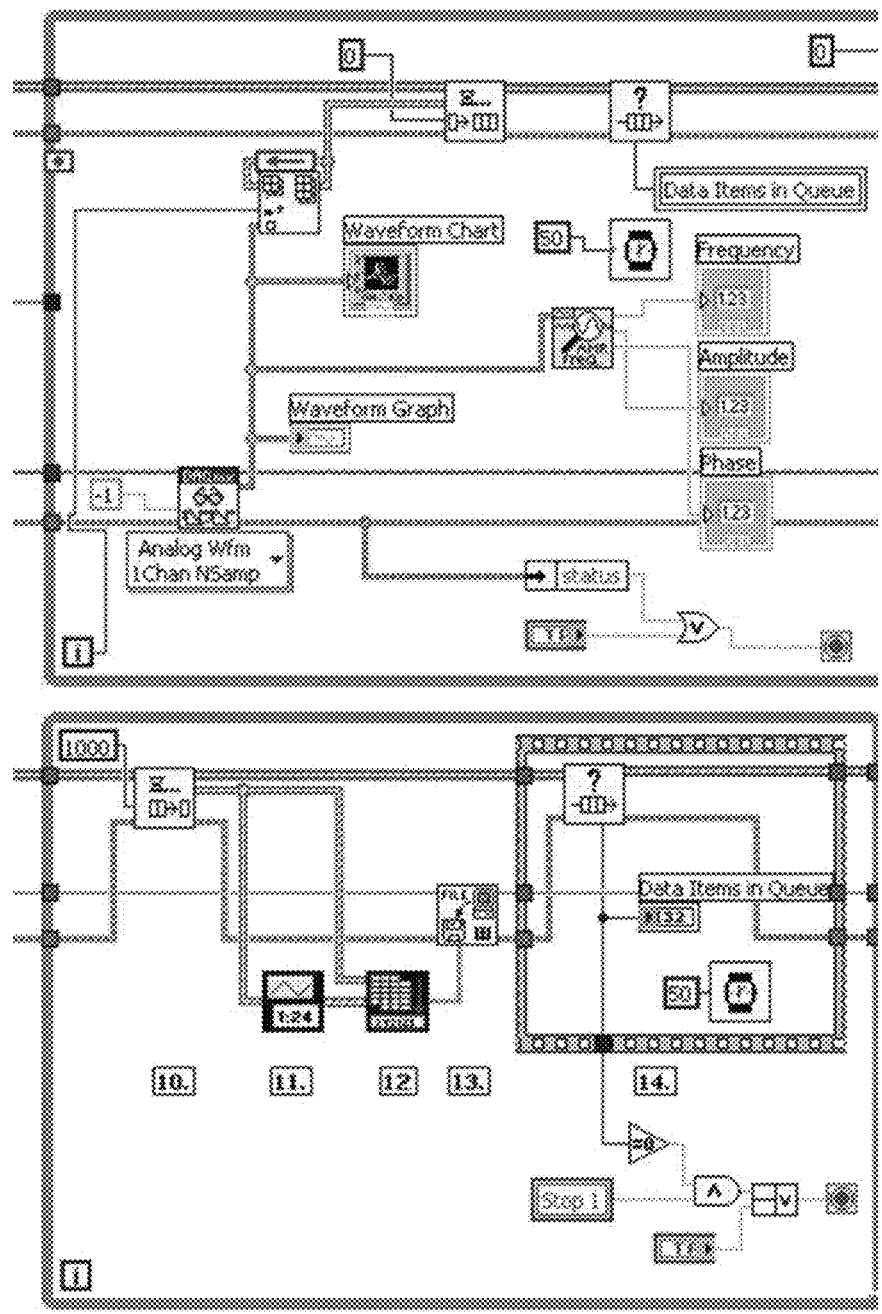
Figure 6C:
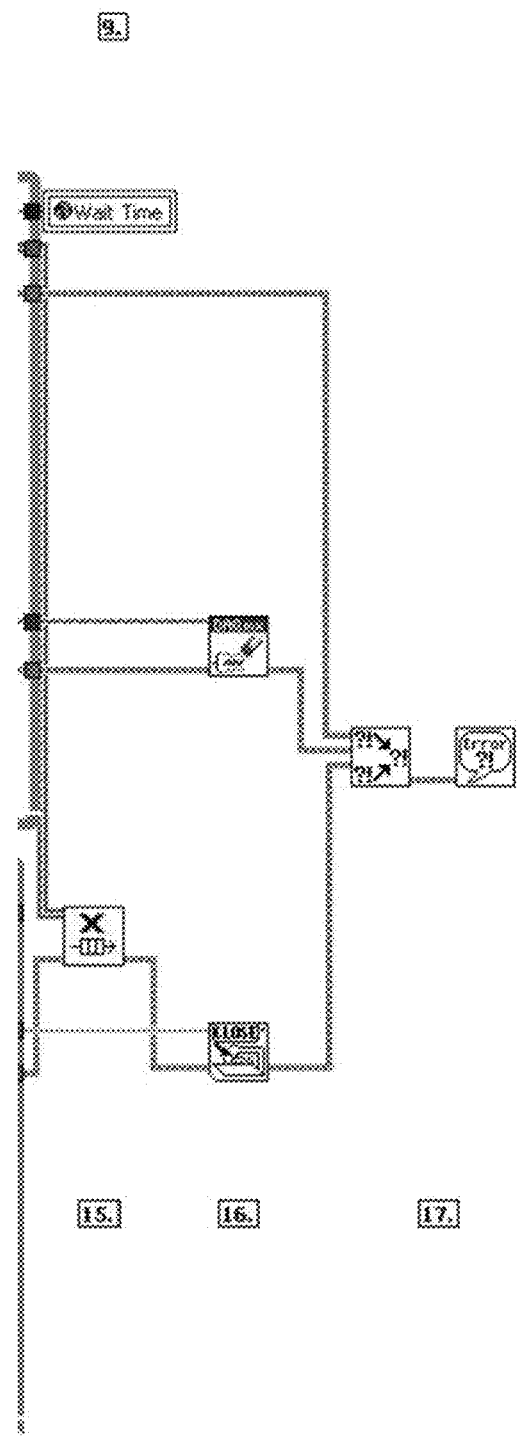

A Labview® (available from National Instruments Corporation, 11500 N Mopac Expwy, Austin, Tex. 78759-3504) computer code was written (see FIG. 6) to automate the data acquisition and analysis to obtain water height measurements directly by the computer using analogue signals from the data acquisition system. The program samples the data acquisition card, saves the data to a file and, in parallel, it processes the data using an autocorrelation program, as outlined in the following program description, in which the numerals in boxes in FIG. 6 are associated with the enumerated steps 1-17.

TABLE 1

The electromechanical measured properties of the LiNbO$_3$ crystals and the Bismuth Titanate with various doping contents [Bar-Cohen et al., 2010].

| Material | T$_C$ (° C.) | K | loss | d$_{33}$ (pC/N) | Q$_p$ | k$_p$ | at 500° C. K | loss | Q$_p$ | resistivity |
|---|---|---|---|---|---|---|---|---|---|---|
| Modified Bi$_4$Ti$_3$O$_{12}$ | 666 | 118 | 0.5% | 16 (16)* | 3000 | 3.7% | 300 | 41% | 200 | 7.4 × 10$^6$ |
| Bi$_{3.887}$Ti$_{2.866}$W$_{0.146}$O$_{12}$—Fe$_2$O$_3$ | ~620 | 154.6 | 1% | 14 (13) | 2900 | 3.3% | 590 | 62% | 50 | 1.5 × 10$^6$ |
| Bi$_{3.9}$Ti$_{2.85}$W$_{0.15}$O$_{12}$—Fe$_2$O$_3$ | ~620 | 156.8 | 1% | 11.5 (11) | 2000 | 3.1% | 670 | 67% | 46 | 1 × 10$^6$ |
| Sr$_{0.8}$Ca$_{0.2}$Bi$_4$Ti$_4$O$_{15}$—Fe$_2$O$_3$ | 595 | 143.7 | 0.4% | 12 (11.5) | 5600 | 2.9% | 461 | 42% | 360 | 1.9 × 10$^6$ |
| Sr$_{0.6}$Ca$_{0.4}$Bi$_4$Ti$_4$O$_{15}$—Fe$_2$O$_3$ | 644 | 146.8 | 0.25% | 8 (8) | 5800 | 2.6% | 463 | 100% | 120 | 2.9 × 10$^5$ |
| Bi$_{3.93}$Ti$_{2.9}$W$_{0.1}$O$_{12}$—MnO$_2$ | 657 | 158 | 0.5% | 17 (11) | 3700 | 4.3% | 421 | 44% | 45 | 3.6 × 10$^6$ |
| Bi$_{3.96}$Ti$_{2.9}$W$_{0.1}$O$_{12}$—MnO$_2$ | ~650 | 145 | 0.3% | 18 (12) | 3900 | 4.3% | 370 | 40% | 40 | 5.6 × 10$^6$ |
| W doped Bi$_4$Ti$_3$O$_{12}$ | 637 | 165.7 | 1.5% | 17 (15.5) | 1800 | 3.4% | 309 | 16% | 1000 | ~5 × 10$^6$ |
| LiNbO$_3$ (36° Y-cut) | 1150 | 62 | 0.5% | 40 (40) | 1500 | 46% | 104 | 6% | 500 | 3.8 × 10$^6$ |

*The value in parenthesis is the data obtained after 500° C.

The reflection signals were processed to obtain the autocorrelation function that is defined as:

$$R_{xx}(\tau) = \frac{1}{T} \int_0^T x(t)x(t+\tau)dt \quad (1)$$

where τ is the time separation variable and T is the sampling period.

Figure 5A:
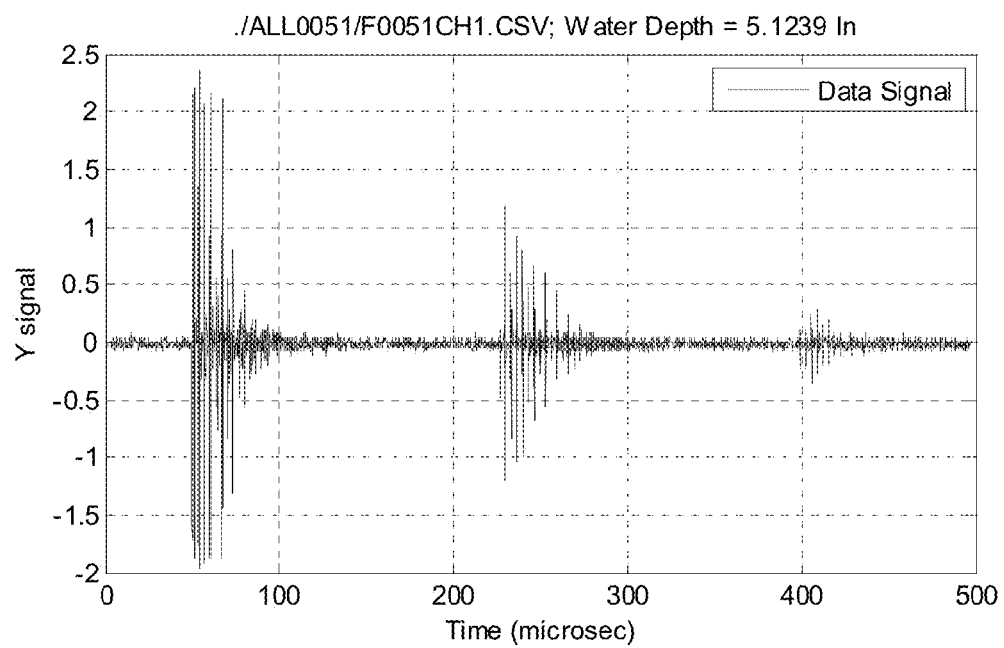
FIG. 5A is a graph illustrating the time of flight showing the first arrival time difference of 179.0 micro second.
Figure 5B:
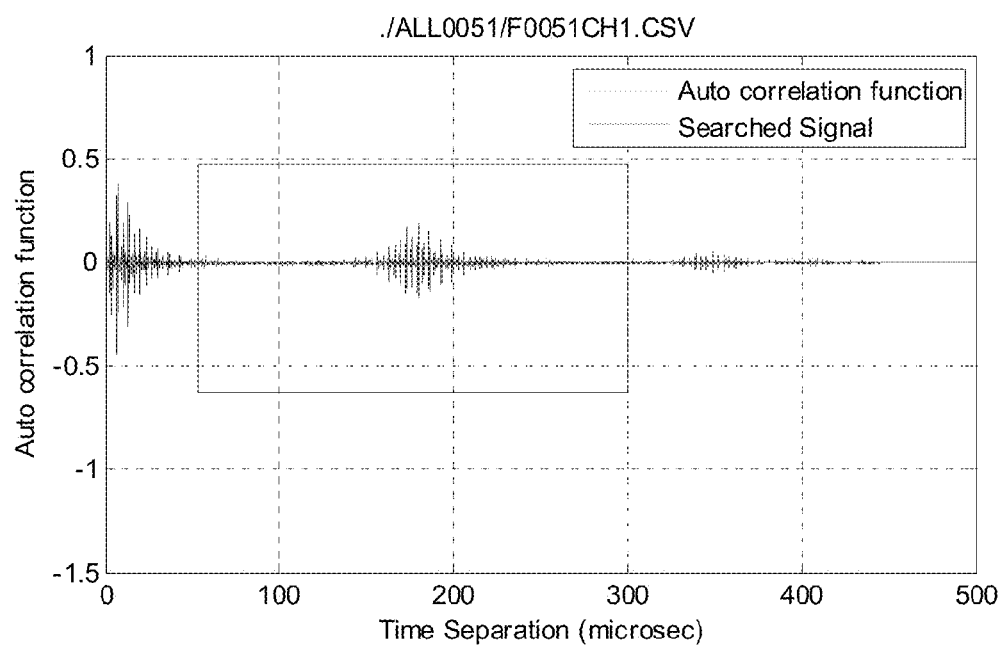
FIG. 5B is a graph illustrating the calculated auto-correlation time difference of 179.6 micro second.

An example of the autocorrelation function is shown in FIG. 5B, where the time of flight was predicted via a predetermined searching window in the calculated autocorrelation function.

Water height measurements for levels of 1.0 to 5.0 inch were performed and the accuracy was found to be quite reasonable having a maximum difference of 6.0% (see Table 2). Some of the error is attributed to the inaccuracy of physical measurement of the water height based on visually measuring LabView® Code Description 1. Sequence structure initializes the program by resetting both stop buttons and setting the wait time that is to be used by the subVIs at steps 11 and 12 to 50 ms.
2. Queue is initialized to pass data between the two loops. A file is opened to store data.
3. Analog input is created.
4. DAQmx Timing VI is used to setup the timing characteristics of the acquisition.
5. The data acquisition task is started. The DAQ card begins acquiring data.
6. DAQmx Read function repeatedly reads acquired data from memory.
7. Enqueue function sends waveform data to the lower loop as it is read.
8. Get Queue Status function returns the total number of items waiting in queue.

9. Once the top loop stops and data acquisition is terminated, the wait times in the subVIs at steps 11 and 12 are changed to 0 ms.
10. Dequeue Element function waits for data provided by Enqueue in the top loop.
11. Waveform Array to Timestamp Array subVI builds timestamps for each data point.
12. Data-Timestamp Arrays to Spreadsheet String subVI converts all acquired data and timestamps into delimited spreadsheet strings to be saved to file.
13. Write File function writes data to file.
14. Get Queue Status updates the number of data items waiting in queue. A time delay is used to ensure that the front panel indicator has time to update despite the fast loop rates inside the subVIs.
15. Queue is closed.
16. The file and data acquisition task are closed.
17. Errors are merged and reported accordingly using a Simple Error Handler.

Figure 7A:
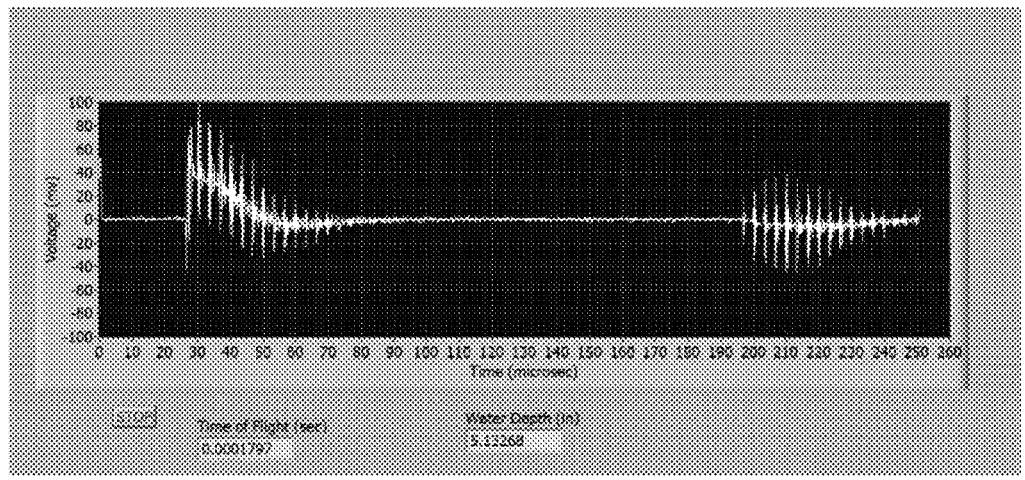
FIG. 7A is a graph illustrating the time-of-flight record generated in real-time.
Figure 7B:
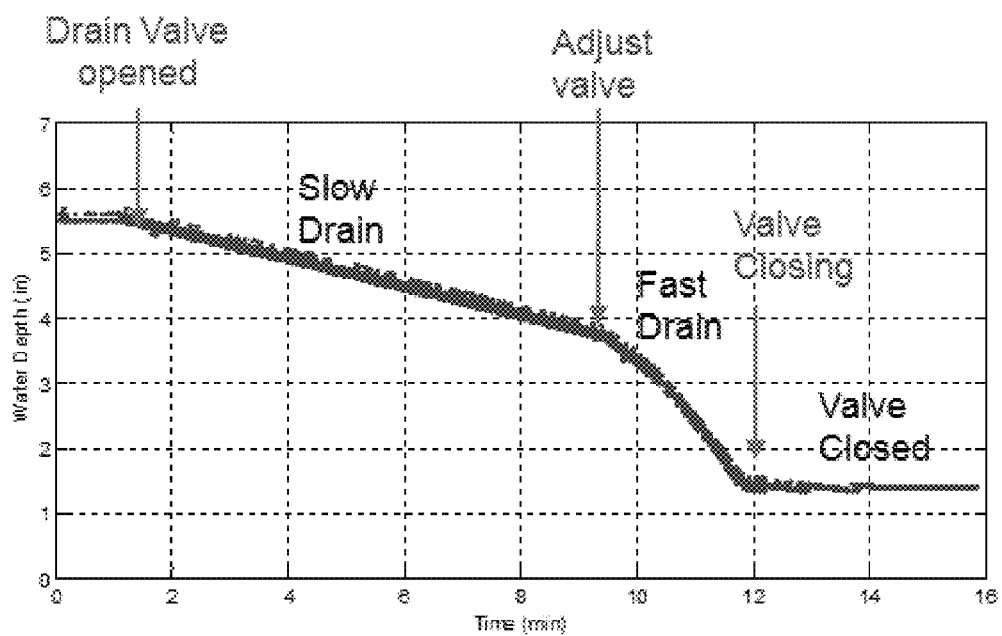
FIG. 7B is a graph illustrating the water height that was determined for fast and slow draining rates.

Using the developed data acquisition and real-time signal processing system, we tested the height of the water in the pipe while draining at two different rates. The results are shown in FIG. 7A and FIG. 7B. The relatively high speed and accuracy obtained validates the feasibility of the developed method. A general purpose programmable computer based system using instructions recorded in machine-readable non-volatile memory can be implemented to perform the data acquisition and analysis.

Surface Perturbation and Bubble Insertion

Figure 8A:
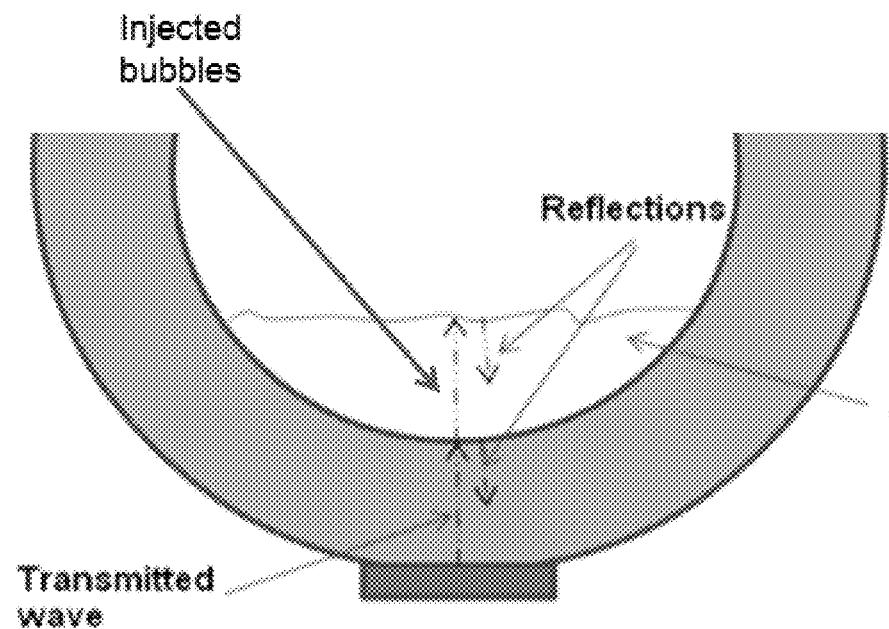
FIG. 8A is a cross-section illustration of the test setup using bubbles.
Figure 8B:
FIG. 8B is an image showing the bubbles that were introduced into the water via the hose seen in the image.

Using the developed automated procedure for measuring the height of the water in real-time, we tested its capability to handle surface and bulk interferences. For this purpose, we introduced surface perturbation by shaping the surface, by rocking the container, and by the introduction of bubbles in the path of the acoustic wave. The intent was to determine the accuracy of the readings/measurement under simulated conditions of cavitation and perturbation due to various causes. For this test, the setup that was used comprised a pipe segment that was covered by welded plates on the two sides, forming a container that allowed direct access from the top of the container surface. A schematic view of the cross-section of the test setup is shown in FIG. 8A while the hose that introduced bubbles into the path of the wave inside the water is shown in FIG. 8B.

Figure 9:
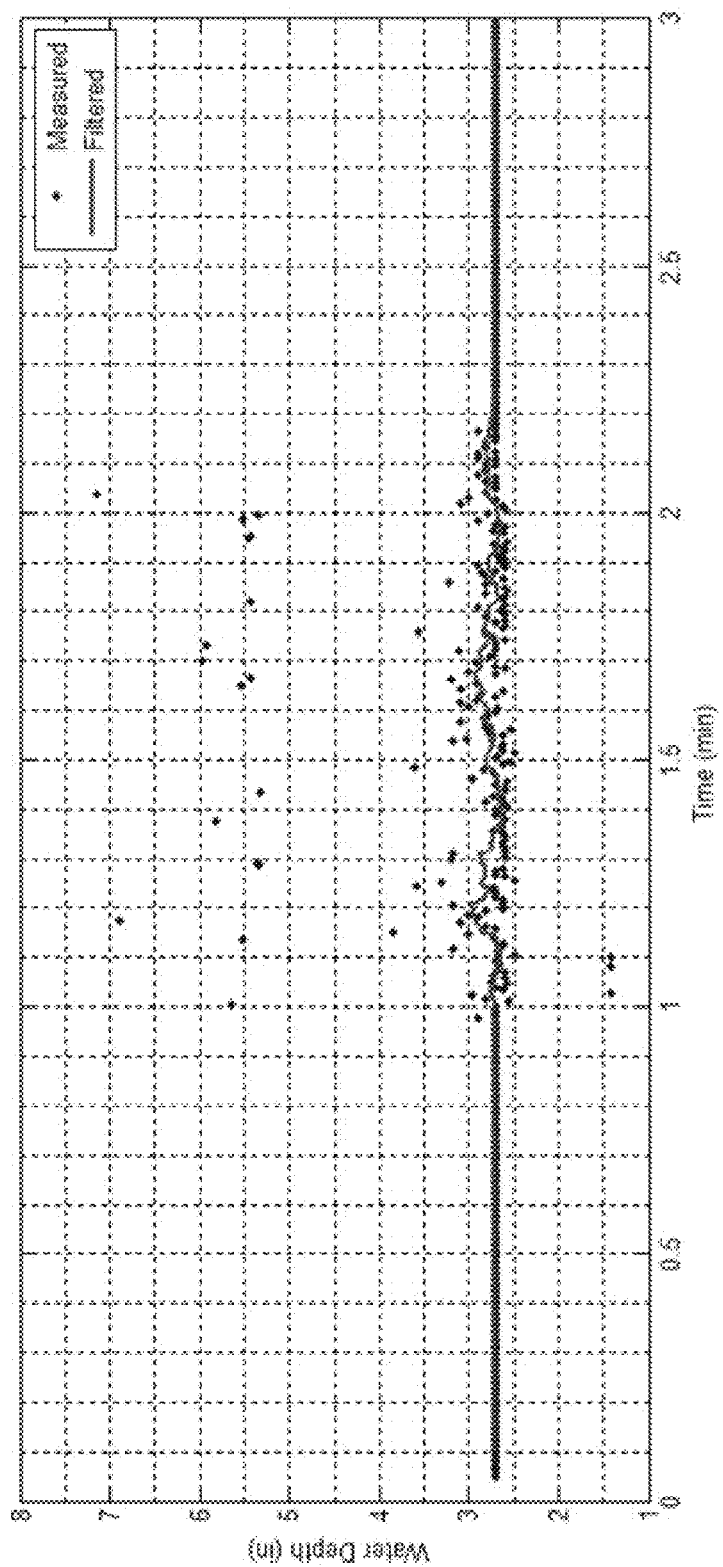
FIG. 9 is a graph illustrating the perturbation from bubbles that were generated 0.5 inch from the bottom of the pipe at 1 inch away from the ultrasonic wave path.
Figure 10:
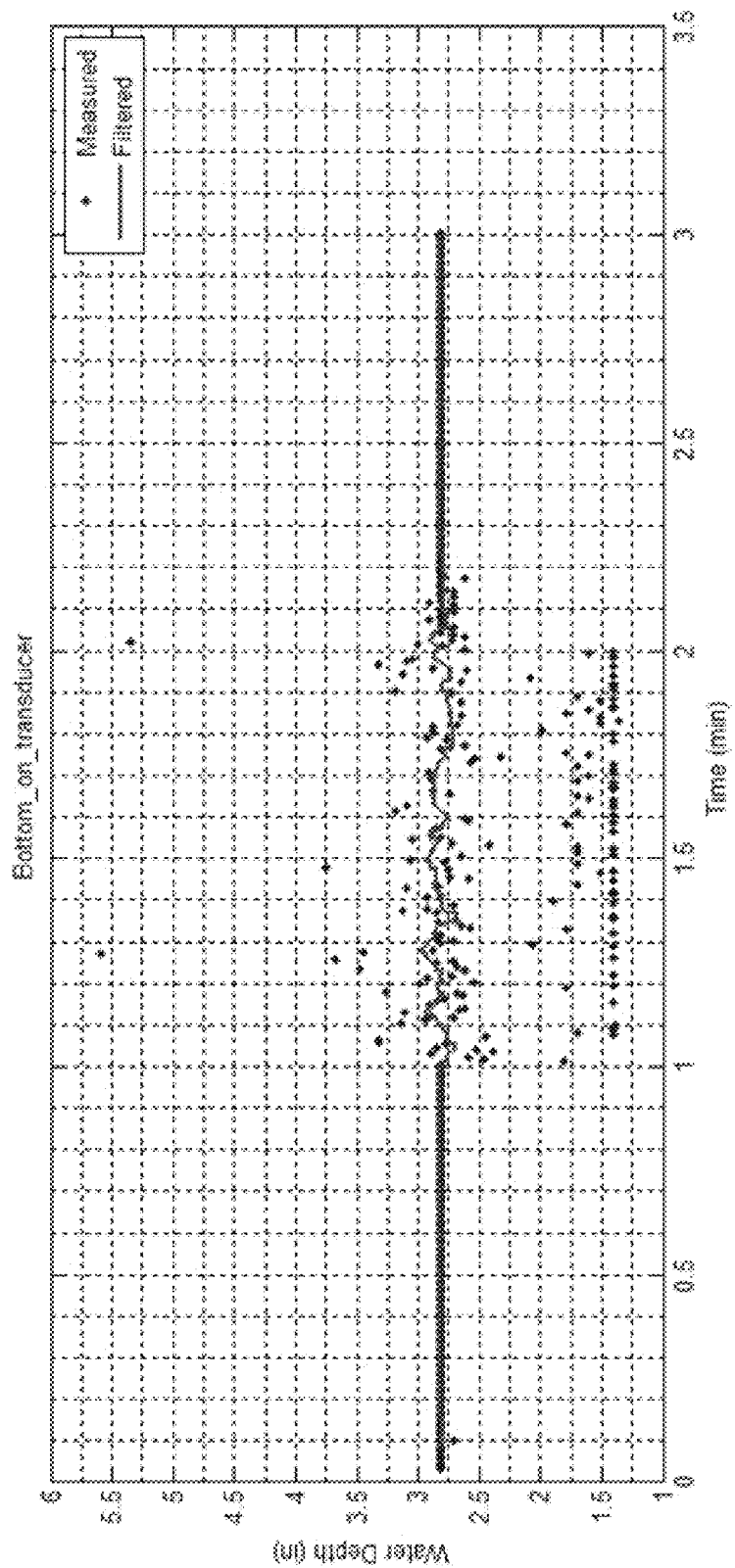
FIG. 10 is a graph illustrating the perturbation from bubbles generated 0.5 inch from the bottom of the pipe directly along the wave path
Figure 11:
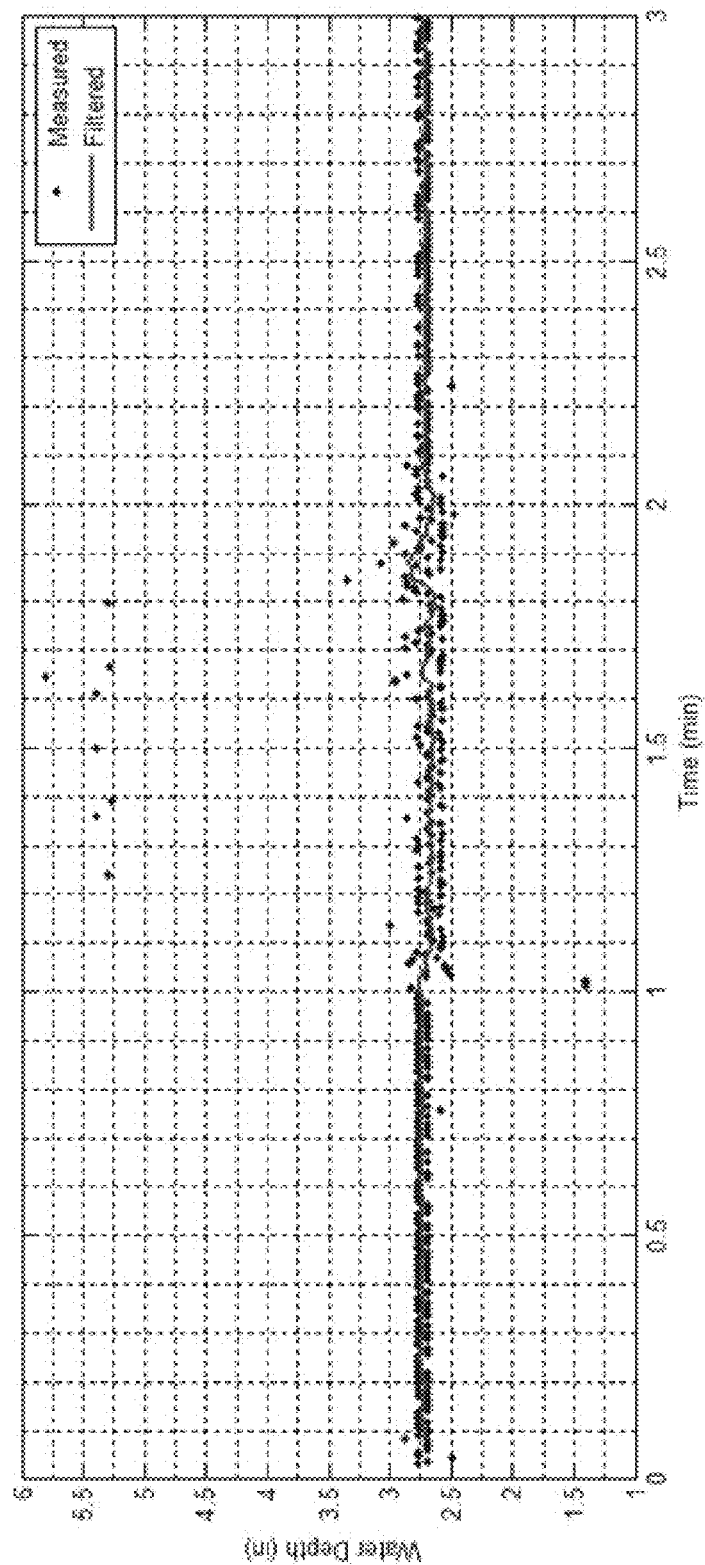
FIG. 11 is a graph illustrating the perturbation from bubbles generated on the surface of the water 1 inch away from the wave path.

Data was acquired as the various perturbation conditions were introduced. Each test comprised one minute of water at "rest", one minute of perturbed water (bubbling or shaking) and one minute of water at "rest" again. The data was acquired while calculating a moving average curve with the outlier data excluded. The bubbles were generation at the rate of about 3 bubbles/sec and the surface wobbling was done at a rate of 2-3 Hz. The data for the conditions of generating bubbles 0.5 inch from the bottom of the pipe surface is shown for 1 inch away from the wave path in FIG. 9 while the data for the case of bubbles emitted along the path shown in FIG. 10. In both cases, there is noisy data received in the window of time that the perturbation was introduced but the running average provided good accuracy of the water height. Another test that was done including generation of bubbles was the introduction of perturbation with bubbles on the surface of the water 1 inch away from the wave path. It is interesting that this data, as shown in FIG. 11, was less noisy than that of other perturbed system tests.

Figure 12:
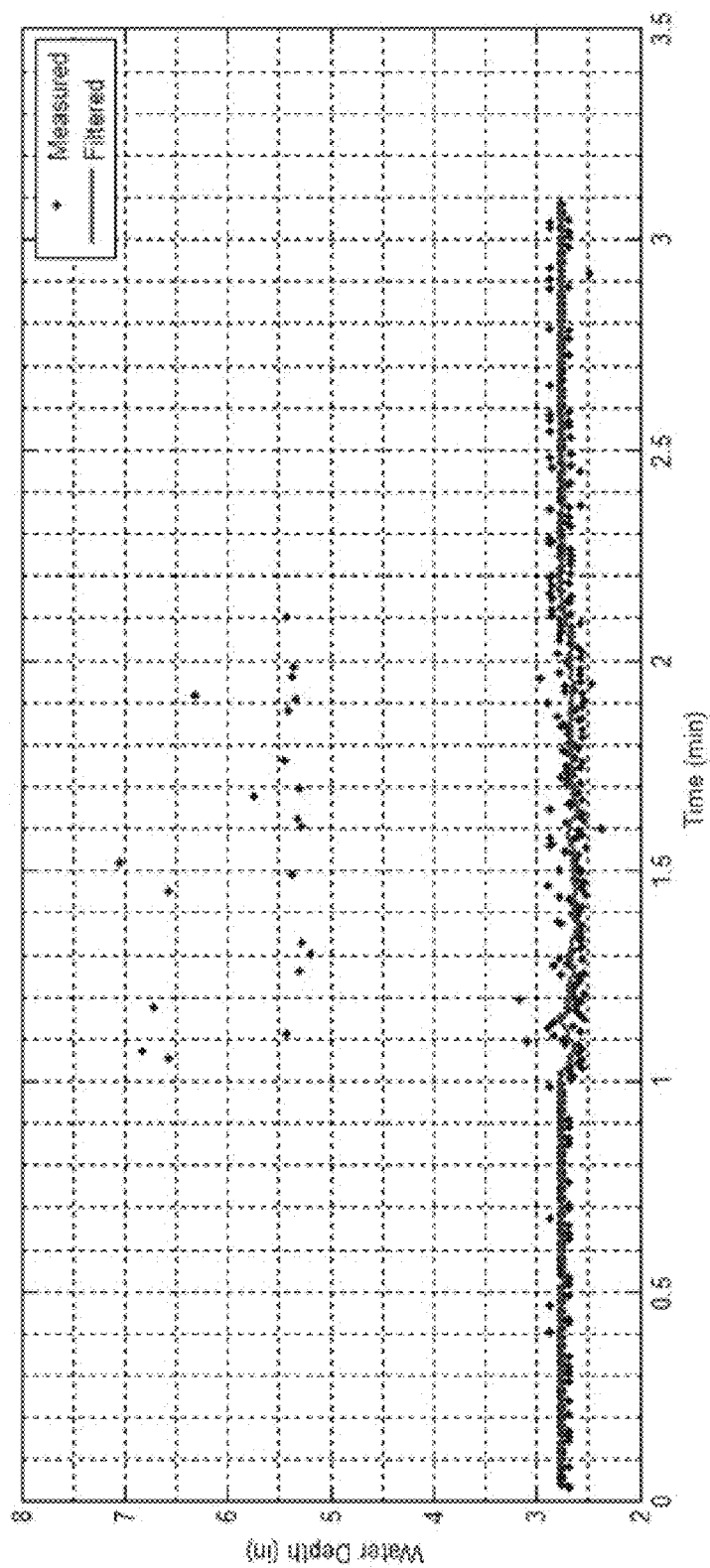
FIG. 12 is a graph illustrating the surface perturbation due to rocking the water container with a wave frequency of ~3 Hz.
Figure 13:
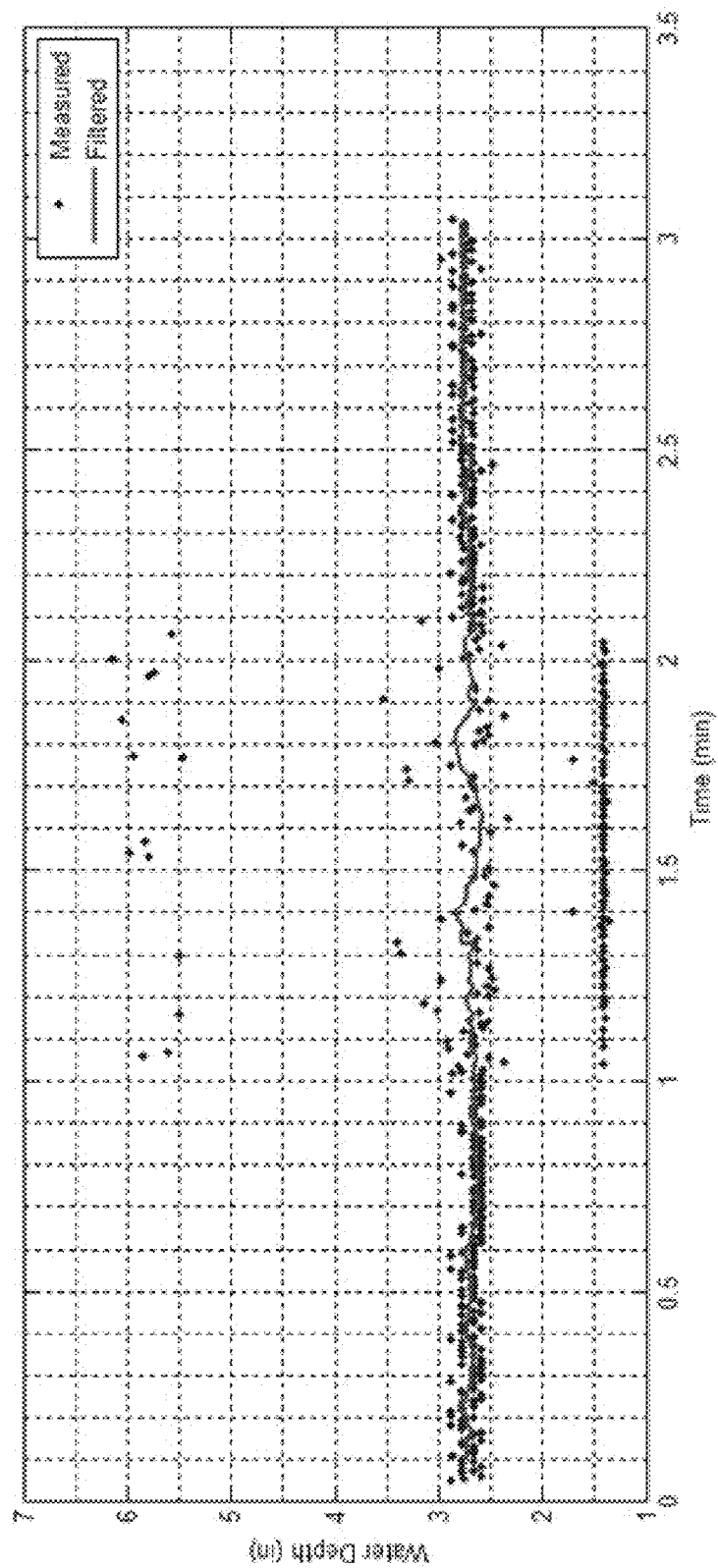
FIG. 13 is a graph illustrating the perturbation by manually shaking the surface of the water using a small bowl that was bobbled in the water, far from the wave path. The surface shaking rate was ~2 Hz.

Following the success of these tests, we introduced direct shaking of the water surface. FIG. 12 shows the results for the case of rocking the water container creating a wave frequency of 3 Hz. In addition, we wobbled the surface by placing a small bowl into the water surface and raising and lowering it manually away from the water path. Again in both cases, while the data was noisy the running average provided good accuracy of the water height.

Figure 14:
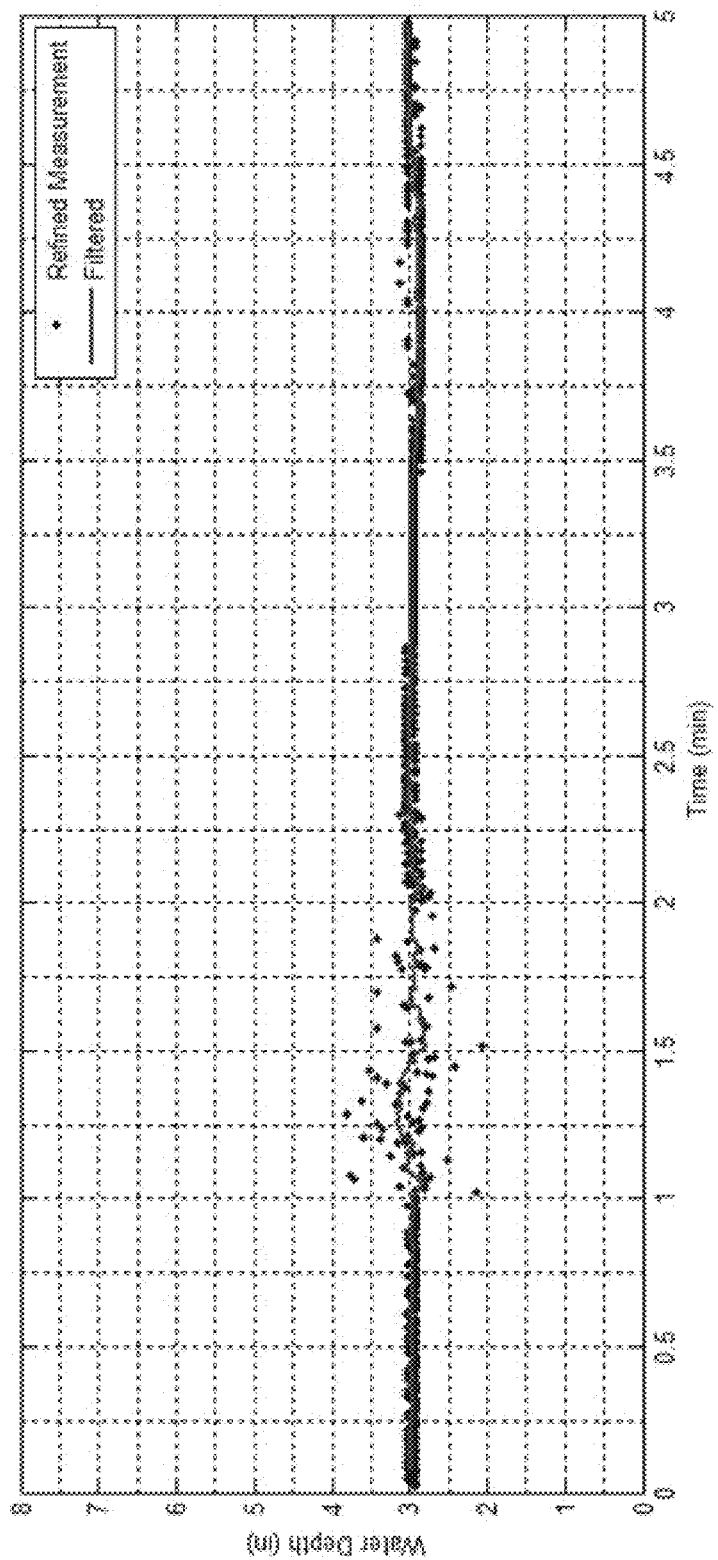
FIG. 14 is a graph illustrating the prescreened data received from the case of the water being perturbation from bubbles generated 0.5 inch from the bottom of the pipe directly along the wave path.

The above results are quite encouraging but they also suggest the need for a smart procedure that is configured to screen data for outliers. It is expected that the procedure can be enhanced so that each datum will be evaluated for its validity in order to make sure that we maximize the use of data using a minimal number of pulses, thus minimizing power consumption. An example of the water height that was measured with the refined process, wherein we prescreen data, is shown in FIG. 14.

Figure 15A:
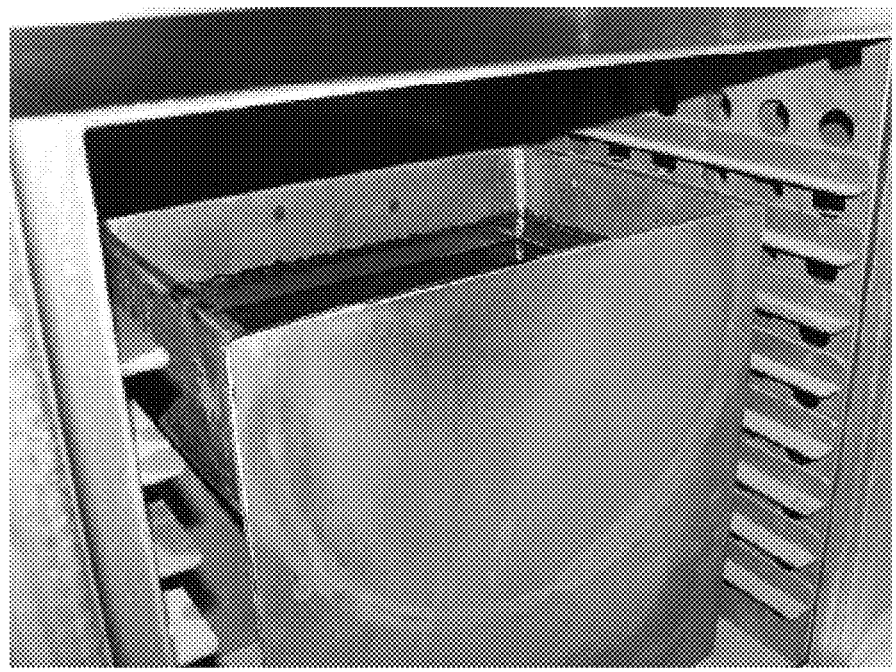
FIG. 15A is an image of the high temperature (HT) test-bed with safflower oil.
Figure 15B:
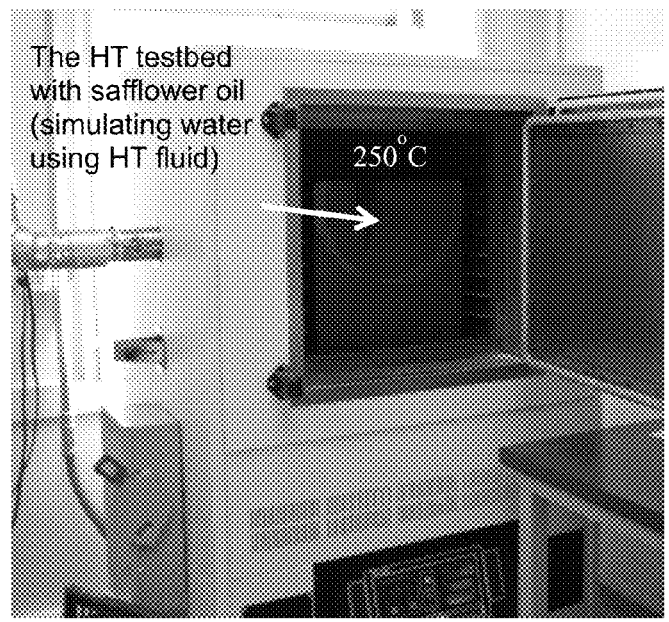
FIG. 15B is an image of the high temperature (HT) test-bed in the chamber where it was subjected to 250° C.

In order to simulate the condition of 250° C., a high temperature chamber was used. The chamber consists of an Ultra-Temp Standard Convection Industrial Oven Model 6680 Ultra Temp (made by Blue M). A HT test-bed comprising a section of the pipe was used to serve as a container (see FIG. 15A) and it was filled with safflower oil as a substitute to condensed water (thus avoiding the risk of having to deal with the safety issues related to operation of steam at high pressure). The tank and the test setting were examined by subjecting the HT test-bed for 2 hours at 250° C. and it was confirmed that the container with the oil sustained the exposure with no damage that could occur due to thermal stresses in the structure or the possibility of the oil boiling. The high temperature test bed is shown in FIG. 15B in the heating system.

Figure 16A:
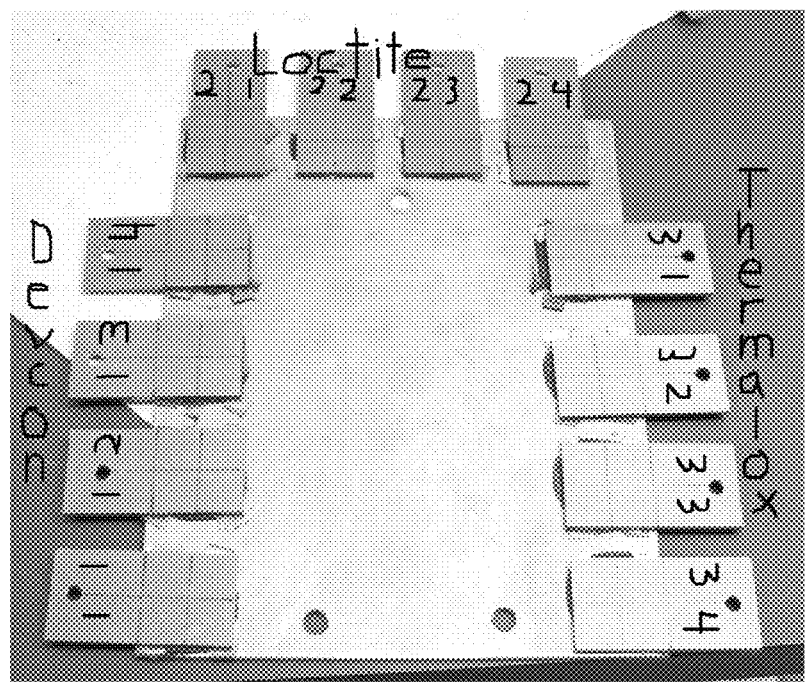
FIG. 16A is an image of the bonded steel coupons that were used to test the effect of exposure to 250° C. using three bonding materials.
Figure 16B:
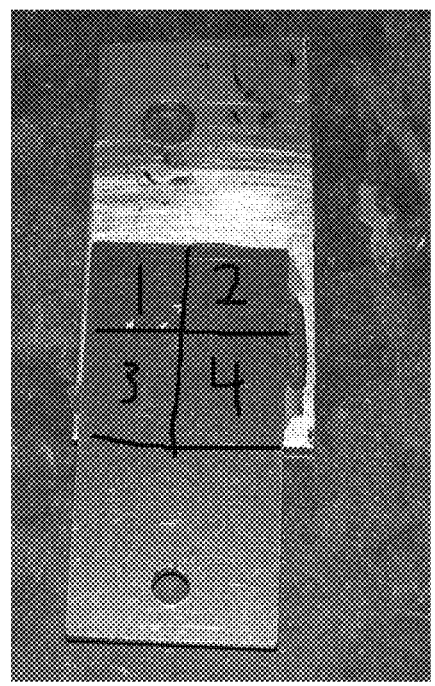
FIG. 16B is an image of the bonded steel coupons that were used to test the effect of exposure to 250° C.

The operation of the transducer in the field requires bonding to the pipe to provide path continuity for the ultrasonic waves. For this purpose, three HT adhesives were tested including Devcon RTV Sealant comprising Silite High Temp. Silicone (ITW Devcon), Loctite comprising Superflex Red High Temp RTV (Henkel Loctite Corporation), and Thermalox High Temp Silicone Sealant comprising 2655 Oxide Red (Dempney Company, Inc.). Bonded steel coupons were made and each bonded area was marked with 4 segments (see FIG. 16A and FIG. 16B) at which the bond was tested before and after the exposure.

Figure 17A:
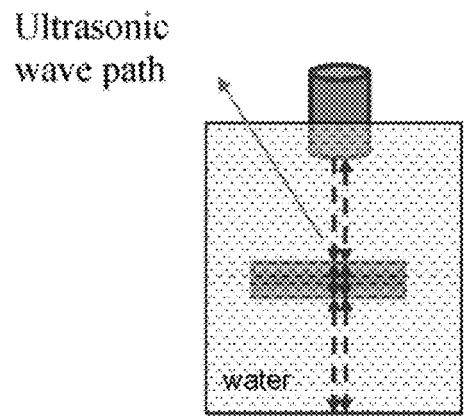
FIG. 17A is a diagram illustrating the test setup for the coupon.
Figure 17B:
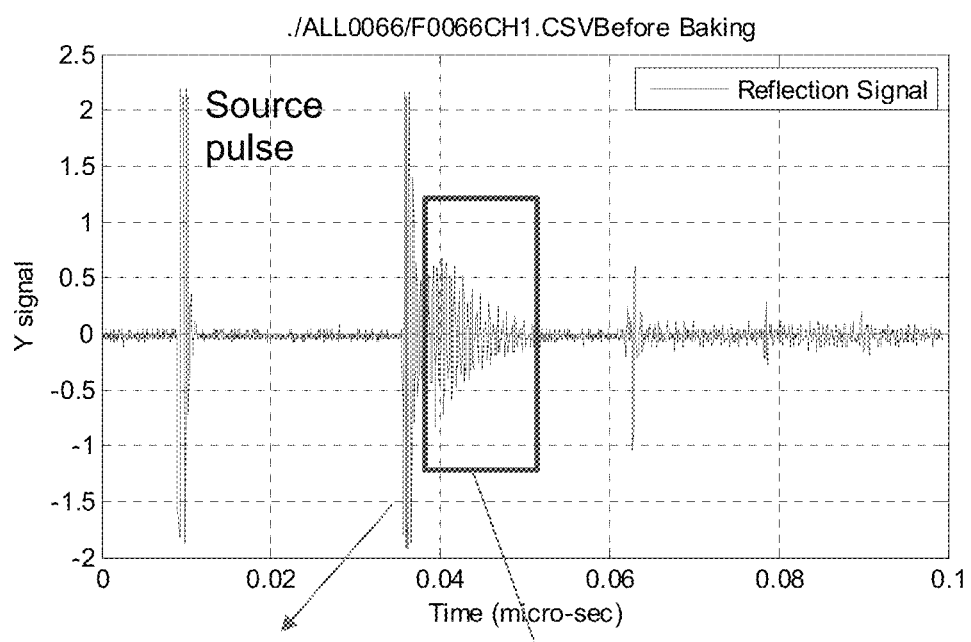
FIG. 17B is a diagram illustrating the reflection pattern for the unbonded coupon.
Figure 17C:
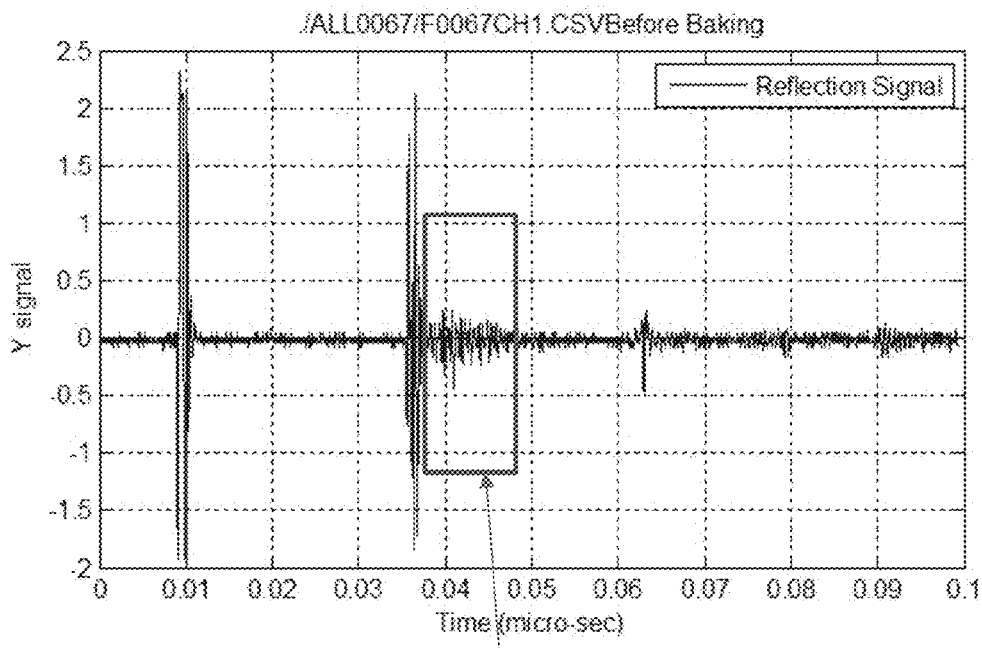
FIG. 17C is a diagram illustrating the reflection pattern for the bonded coupon.
Figure 18:
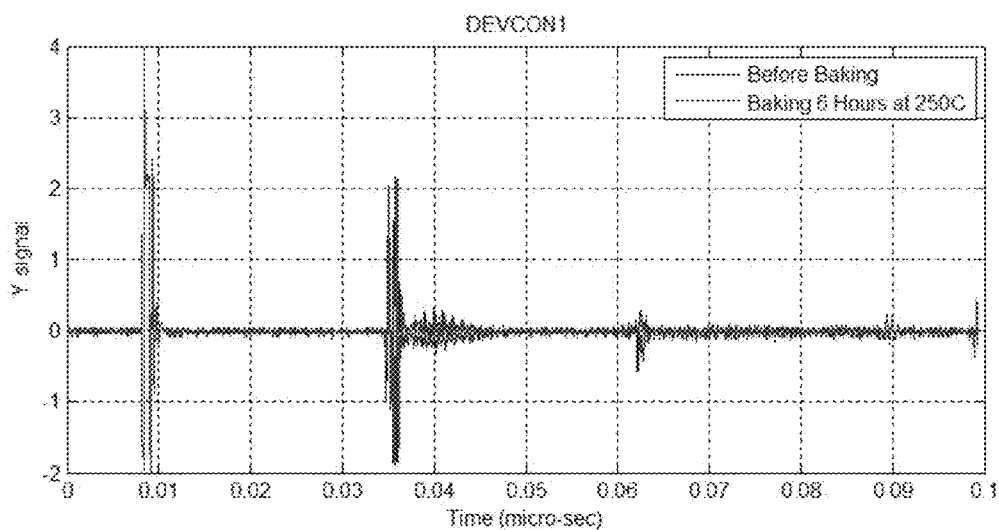
FIG. 18 is a diagram illustrating the signals from the bonded coupon with the Devcon adhesive before and after exposure to 250° C. for 6 hours.
Figure 19:
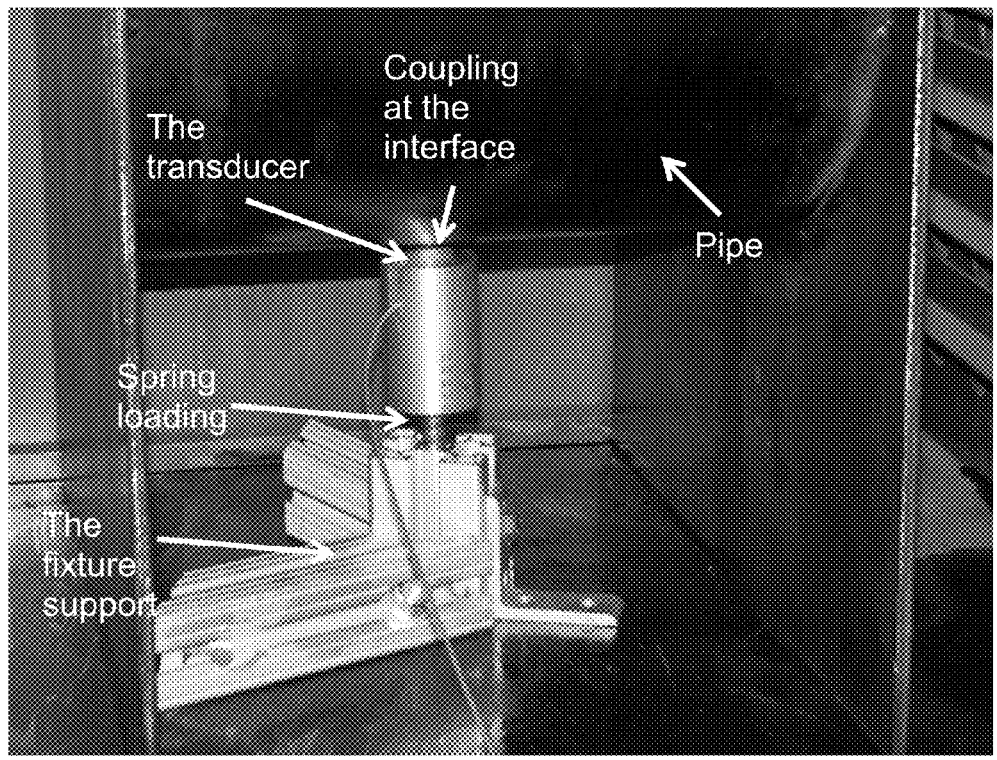
FIG. 19 is an image illustrating the HT mounting of the transducer allowing pushing it against the pipe at the high temperature tests.
Figure 20:
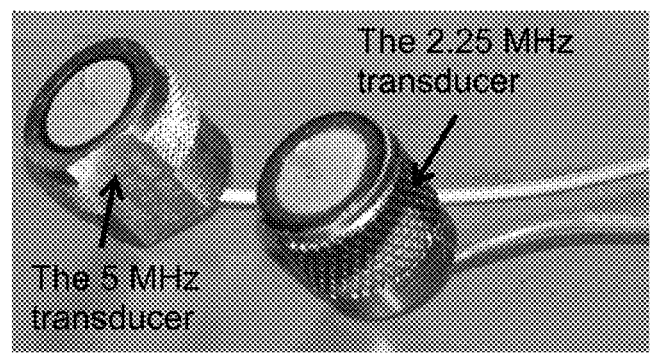
FIG. 20 is a diagram illustrating the 5 and 2.25 MHz Transducers. The color change at the top of the 2.25 MHz transducer is the result of the exposure to 250° C.
Figure 21A:
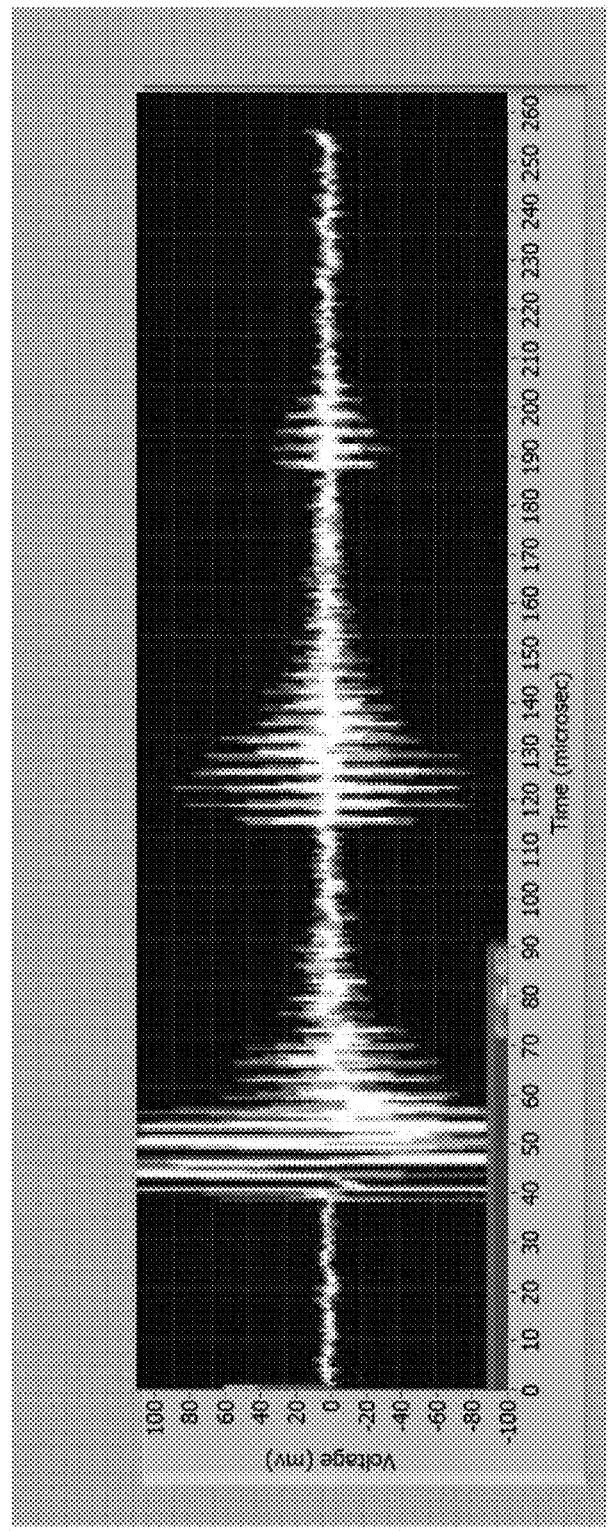
FIG. 21A is a graph illustrating the reflection pattern at room temperature that was received from the top surface of the safflower oil.
Figure 21B:
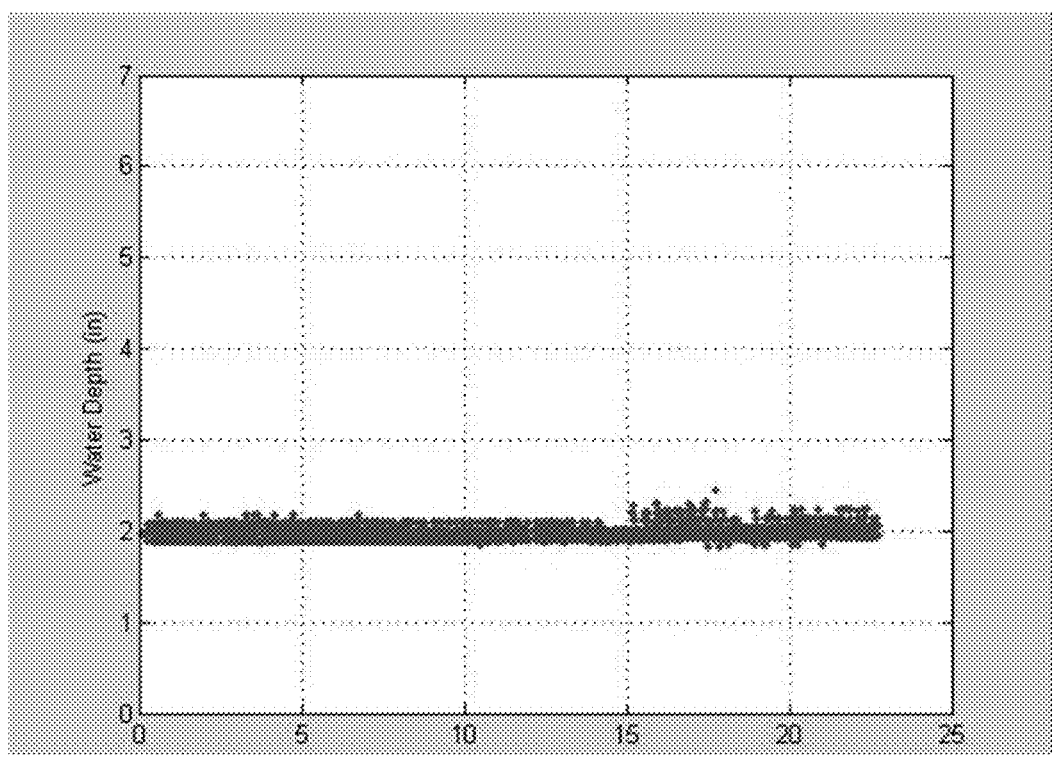
FIG. 21B is a graph illustrating the measured height of the safflower oil. The transducer used was a 2.25 MHz, 0.5 inch diameter device made by Sigma Transducers.
Figure 22:
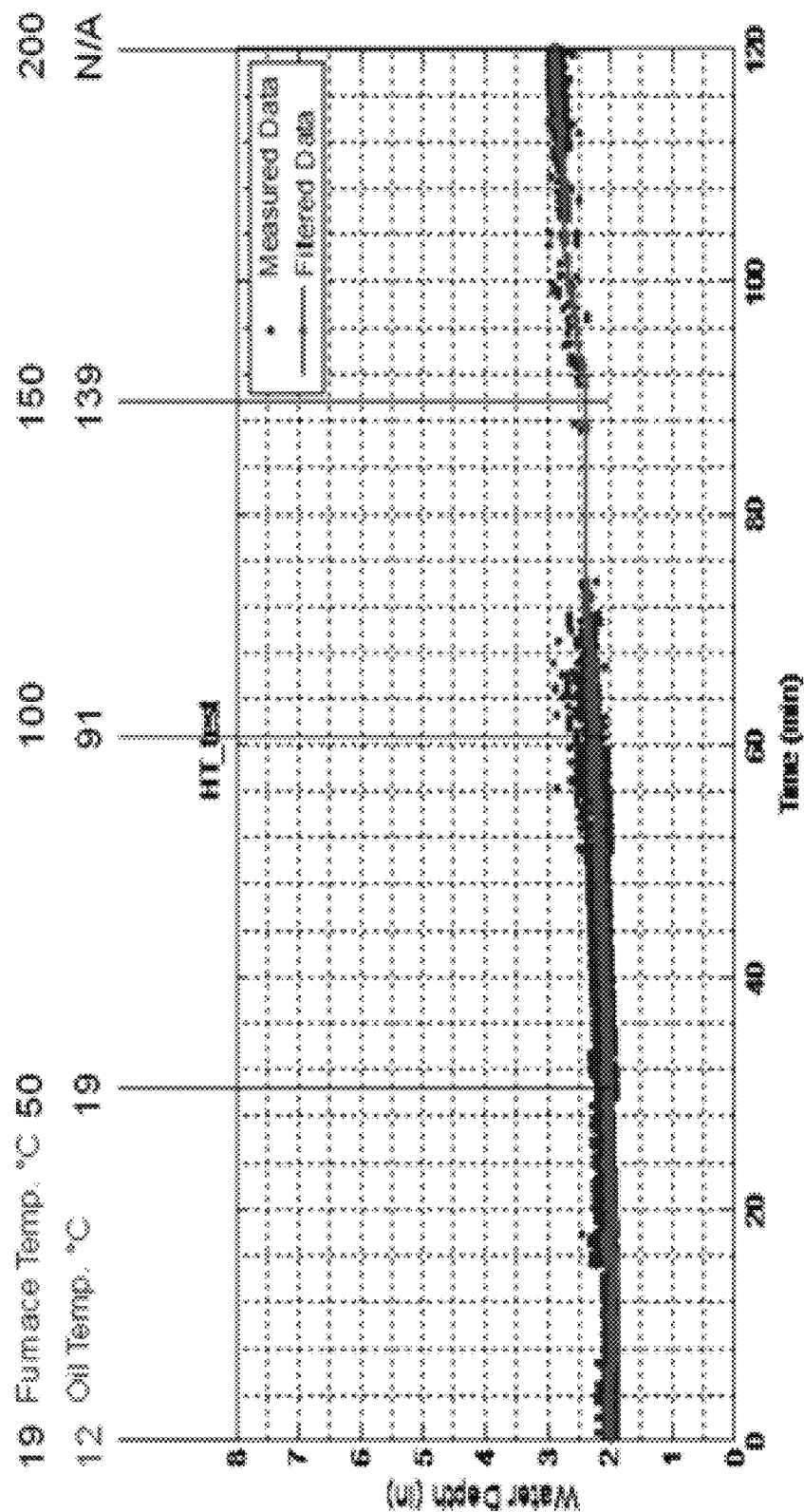
FIG. 22 is a graph that illustrates the measured height as a function of time and the temperature in the oven and the safflower oil. The dots are the data readings and the line is the average.

To determine the bond integrity, a pulse-echo test was done on unbonded and bonded steel coupons. A schematic view of the test setup and the reflection patterns are shown in FIG. 17A, FIG. 17B and FIG. 17C. The boxed section on the reflection pattern shows the ringing that results from multiple reflections inside the unbonded plate. The reflected ultrasonic signals were measured for the coupons after bonding and significant damping of the ringing has been observed when the sample bond integrity is sound (FIG. 17C and FIG. 18). It is contemplated that a method of attachment of the piezoelectric transducer that provides for clean entry of the emitted ultrasonic signal through the steam pipe wall is provided, so that the reflected signals from the interface between the interior wall of the steam pipe and condensed liquid and from the interface between the condensed liquid and gaseous steam are observable with minimized interference from reflected signals from the interface between the exterior of the steam pipe and the bonded piezoelectric transducer. In one embodiment, bonding the piezoelectric transducer with a substance that provides a continuous path having a density higher than air (such as provided by a bonding medium that is a solid when cured) is contemplated. In addition, provision of a mechanical attachment to reduce stress on the bond, such as by strapping the bonded piezoelectric transducer to the exterior of the steam pipe, or provision of some other mechanical support, such as a threaded fitting attached to the exterior surface of the steam pipe that connects to a corresponding threaded portion of the piezoelectric transducer body, is contemplated.

While the tests of the three adhesives after exposure for 2.5 hours indicated no loss of the adhesion integrity, the results after further exposure up to another 6 hours showed the failure of the Loctite while the other two maintained bonding integrity.

The technology is applicable to steam pipe systems and the critical safety issue that it addresses should make its commercialization quite attractive.

Deployment Environment Assessment

The problem that is solved presented a set of multi-variant challenges to the system design. Among the issues considered were:

Location and Access

The system preferably should be easily deployable and serviceable since the man-hole access underground is limited, thus weight and volume have to be kept as low as possible. Also, because of the difficulty of access, wireless remote and local on site diagnosis and monitoring capability are highly desirable.

Thermal Environment

Based on onsite temperature measurements, several thermal zones around the steam pipe were defined. Just below street level the temperature is estimated at ~55° C. (130° F.). The wall temperature inside a manhole was measured at ~65° C. (150° F.). The temperature of the ambient air in a manhole was measured at ~95° C. (200° F.). The steam pipe zone temperature was estimated at ~202° C. (400° F.).

Since the temperature of the exterior steam pipe wall in the manhole is approximately 202° C., and the transducer is indirectly attached to the pipe, a worst case operating temperature for the electronics of 220° C. was assumed. Therefore, for the design purposes (i.e., to provide sufficient margin), 250° C. was chosen as the maximum temperature.

Chemical Environment

Based on empirical data, the chemical environment around the pipe is extremely corrosive. Attention should be paid to both external packaging and connector sealing of internal components and wiring.

Humidity

Based on empirical data, it is assumed that the relative humidity in the manhole is 100%.

Sensory Input and Output Requirements

The piezoelectric transducer requires a 200 Vpeak pulse to generate the desired acoustic signal. In order to minimize any noise pickup and interference, the low level electrical signal generated by the piezoelectric transducer as a result of the received reflected acoustic signal preferably should be amplified as closely as possible to the transducer location.

Safety and High Voltage Confinement

Since the physical distance from the signal processing module electronics to the transducer electronics is expected to be approximately 20-30 feet (or approximately 6-10 meters), it is advantageous to generate the high voltage needed for the transducer locally, i.e., at the transducer electronics location and not at the signal processing module electronics location. By doing this, it is expected that one can minimize the signal degradation and the radiated/conducted noise, as well as the risk of injury to installation and maintenance personnel. The signal processing module and the transducer electronics can be powered using any convenient common electrical power supply or individual power supplies.

Ease of Deployment

Since the final system implementation entails the deployment of up to one thousand or more of these sensor systems, affordability considerations mandate that the system elements have identical hardware, be uniquely identifiable and be remotely or locally (re)configurable.

Instrumentation and Water Height Measurement Methodology

A piezoelectric transducer is expected to emit an ultrasonic signal as a probe signal to sense the condition of the fluid contents of the steam pipe. A portion of the mechanical energy that is imparted to the pipe system is expected to be reflected back to the same transducer. The induced mechanical vibration within the transducer is expected to produce a low level electrical signal. This electrical signal preferably is amplified and transferred to the signal processing module electronics.

The amplified analog signal from the transducer electronics is filtered and re-amplified before it is introduced to a high resolution Analog to Digital Converter (A/D converter or ADC) for digitization. The digitized data is stored in an onboard memory and signal processing is then performed on the data. The mathematical operations are expected to isolate and extract the water height signal from the complex back echo signature.

To conserve power and bandwidth, it is expected that if power is limited, the continuously acquired measurements are not expected to be broadcast every second, but rather every few minutes or on an as-needed/as-commanded basis. If power is not a limitation, the acquired measurements can be broadcast on any convenient schedule, ranging from continuous broadcasting to broadcasting on a schedule, with the expectation that conditions that require immediate or foreseeable attention will be announced as soon as they become apparent. They are expected to be packetized and burst transmitted to a central location. The measurement results are expected to be evaluated by being binned in three ranges, one in which the readings are normal or unremarkable, one in which the readings are at or near limiting values of the normal range, and one in which the readings are anomalous (e.g., beyond a normal value range) and indicate that a problem is imminent or has actually occurred. In the event of a water height reading anomaly, the system is expected to broadcast an alarm, send a data burst containing the pre-event readings, and then transmit continuous readings for a predetermined time interval. In another embodiment, a local connection can be provided to allow display and recording of the data at the site where it is generated.

Signal Processing

We now describe a system and method for analyzing wave reflections and time of flight ultrasonic pulse-echo data for monitoring the health of steam pipes to determine the height of condensed water through the wall in real-time. The system and method involve an algorithm was computer coded for measuring the height.

It is believed that the novel features of this system and method include a signal processing algorithm and computer code for determining the height of condensed water thru the wall of a steel pipe, and an effective analytical means of extracting time-of-flight data from noisy signals.

The computer code that embodies the algorithm provides an effective method of analyzing time of flight ultrasonic pulse-echo data in nondestructive evaluation (NDE) and health monitoring applications. Such systems and methods are needed to help determine the quality and integrity of structures. This includes the ability to detect minute flaws that are critical to detect and secure the operation of structures in service.

An effective in-service health monitoring system and method is needed to track water condensation in real-time through the wall of the steam pipes. The system is required to measure the height of the condensed water from outside the pipe while operating at temperatures that are as high as 250°

C. The system needs to account for the effects of water flow and cavitation. In addition, it is desired that the system does not require perforating the pipes and thereby reducing the structural integrity. The determination of the height requires analysis of small amplitude reflections and complicated echo patterns.

The disclosed software is computer code for determining the height of condensed water thru the wall of a steel pipe that embodies a signal processing algorithm. Various signal processing techniques including the auto correlation method, the Hilbert transform, and the Shannon Energy Envelope methods were studied and implemented to determine the of water height in steam pipes. The results have shown that the developed method provides a good capability for monitoring the height in regular conditions. An alternative solution for shallow water or no water conditions based on a developed hybrid method based on Hilbert transform (HT) with a high pass filter and using the optimized windowing technique is described.

A metropolitan steam system is a district heating system which takes steam produced by steam generating stations and carries it under the streets to heat, cool, or supply energy to factories, buildings, and businesses. It is advantageous to monitor such systems to assure the safe operation of the system. Under certain conditions, the steam system may accumulate condensed water inside the pipe system. Excessive rise in the height of water in the pipe is a source of concern due to the possible generation of water hammer effects that may lead to adverse consequences including damaged vents, traps, regulators and piping. The water hammer effect is caused by the accumulation of condensed water that is trapped in horizontal portions of the steam pipes.

We have developed and demonstrated the feasibility of using an ultrasonic based technique of monitoring the condensate height that sustains the harsh environments of the steam pipe system (<250° C.). The nondestructive measurement technique is based on the Pulse-Echo method of using the time-of-flight of the wave reflections from the top surface of the water to calculate the water height as illustrated in FIG. 1.

Figure 23:
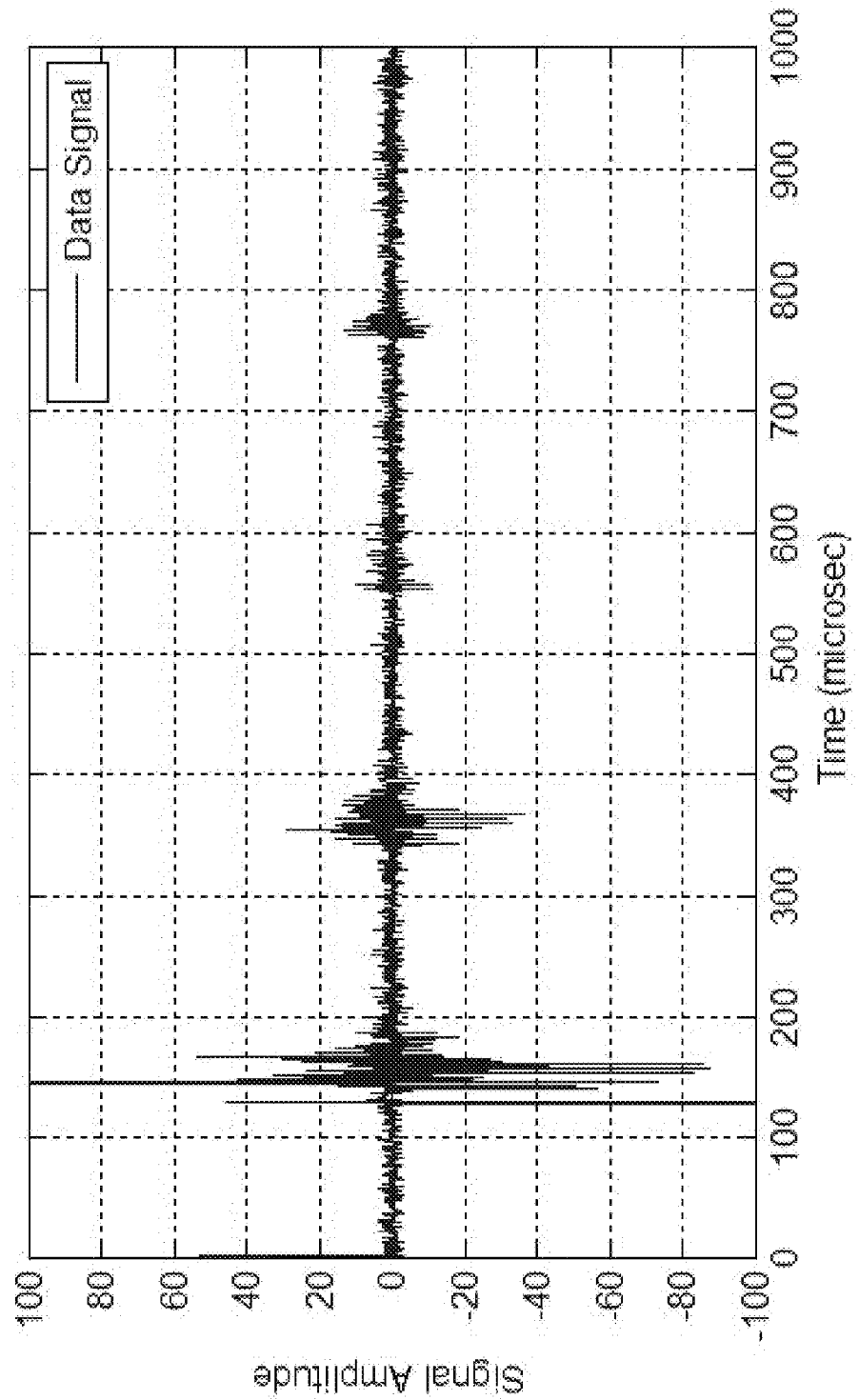
FIG. 23 is a graph illustrating a typical reflection signal from the pulse-echo system.

Typical pulse-echo reflection signals from the reflections of the water inside the pipe are shown in FIG. 23. FIG. 23 is a graph illustrating a typical reflection signal from the pulse-echo system. The numerous reflections that are received in the Pulse-Echo method require effective signal processing techniques to distinguish the reflections from the top and the bottom surfaces of the condensed water.

Generally, there are several issues that need to be taken into account including the strong ringing from the interfaces of the steel pipe, the effect of the pipe curvature that cause wave losses, and the associated attenuation. Also, for practical applications, the received signal may be unstable due to the disturbance of the water surface, external noise, temperature variation, turbulence of the water flow, scattering from potential sediments in the bottom of the pipe inner surface along the path of the wave, or presence of bubbles.

Figure 24B:
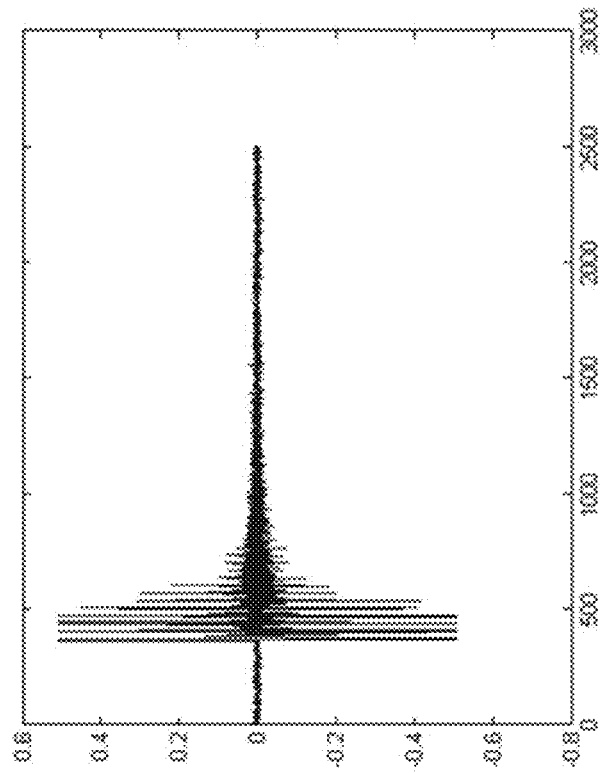
FIG. 24B is a graph showing the reflected signals from the water surface when the surface is wavy.
Figure 24A:
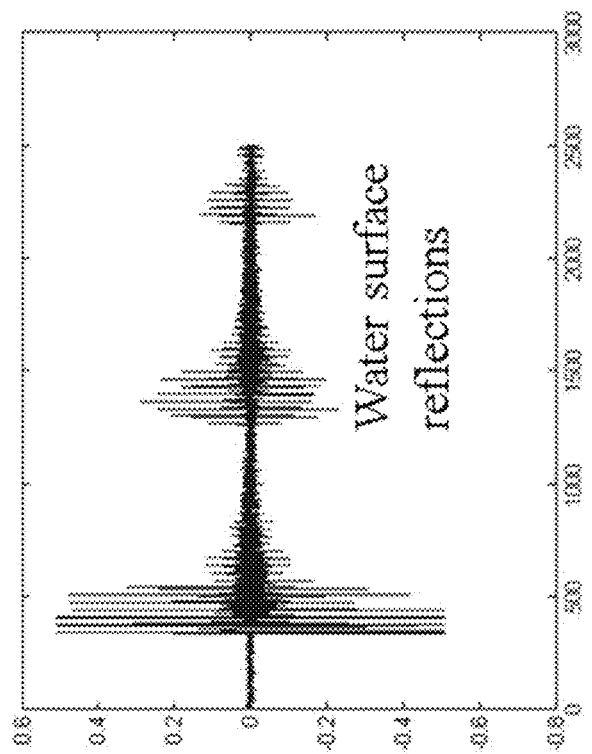
FIG. 24A is a graph showing the reflected signals from the water surface when the surface is steady.

FIG. 24A is a graph showing the reflected signals from the water surface when the surface is steady. FIG. 24B is a graph showing the reflected signals from the water surface when the surface is wavy. FIG. 24A shows reflections from a steady surface whereas in FIG. 24B the water surface reflections are shown to vanish when extremely high waviness is introduced. These issues will cause the loss of fidelity of received signals and make the estimation of the water height difficult. Characteristic of this condition is the variability in the amplitude of the surface reflections. Thus, a reliable signal processing code is needed that comprises windowing, tracking and filtering the reflected signals to obtain stable readings.

The Signal Processing Methods
Characterization of the Time-of-Fight

The measurement of the time-of-fight was developed based on information signal processing theory such the autocorrelation, Hilbert Transformation, and the envelope determination techniques. However, in general, because the temporal and boundary conditions can vary, the application of the techniques may need to be adjusted to be applicable to different fields such as medical, aerospace engineering, civil or mechanical engineering applications. To improve the capability and reliability for the in-situ measurement of liquid inside the pipe, it is advantageous to have a cost-effective method to measure the time-of-flight from the reflected signals. For this purpose, different approaches including autocorrelation, Hilbert Transformation, and Shannon Energy Envelope methods were investigated.

Autocorrelation Method

Figure 26:
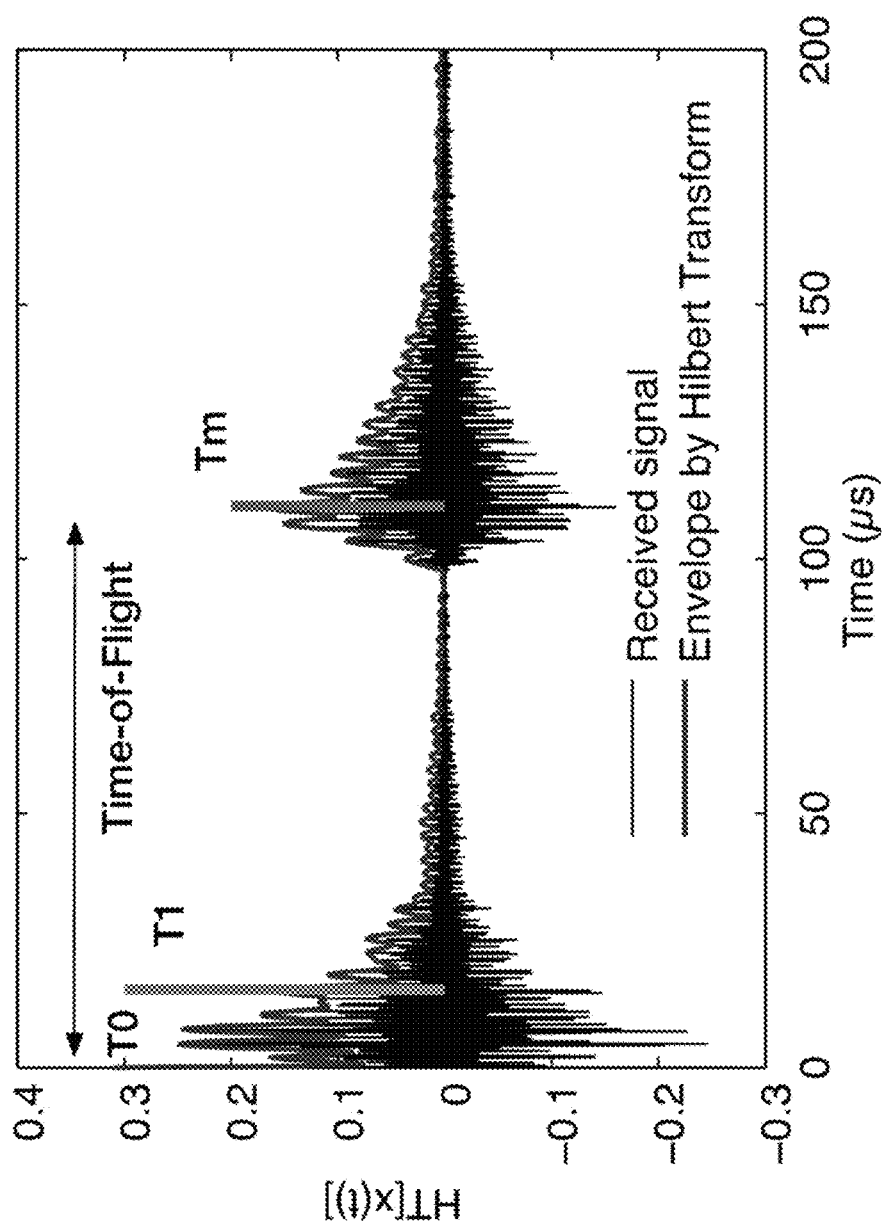
FIG. 26 is a graph showing the received signal and the signal envelope obtained after application of a Hilbert transform, in which $T_0$, $T_1$ and $T_m$ are the peak time from the pipe wall, threshold time and the peak time from the water, respectively.

FIG. 26 is a graph showing the received signal and the signal envelope obtained after application of a Hilbert transform, in which $T_0$, $T_1$ and $T_m$ are the peak time from the pipe wall, threshold time and the peak time from the water, respectively. A large number of reflections that are received from the pipe from a typical test are shown in FIG. 26. Therefore, it is difficult to determine the height using simple time-of-flight measurements in real time. To ameliorate this situation, an auto-correction technique was developed. Auto-correction is one of the most widely used signal processing methods to find repeated patterns or time-of-arrival in the presence of noise. The autocorrelation function given earlier is repeated here for the convenience of the reader:

$$R_{xx}(\tau) = \frac{1}{T} \int_0^T x(t)x(t+\tau)dt \qquad (1)$$

where $\tau$ is the time separation variable and T is the sampling period (or the total sampling time).

An example of the autocorrelation technique is summarized here. The time history of the pulse-echoed signal for testing the water height inside the pipe is shown in FIG. 5A and FIG. 5B. Note that a significant number of reflections are received from the pipe wall (the first set of reflections). The received signals are further complicated by the multiple reflections within the water itself. This large number of reflections makes it difficult to base the determination of the height on simple time-of-flight measurements. An auto-correction of the signal, where the autocorrelation leads to a first maximum group in the initial time stage at t=0 then decay out at a certain period of time is shown in FIG. 5A. This group 1 maximum autocorrelation is associated with the ringing signal from the pipe wall. We obtained a second local maximum at time t=τ, when the backscattered echoes are separated by a time delay. The time τ, thus, corresponds to a time delay between two successive echoes, corresponding to the time-of-fight (TOF) of the ultrasonic waves through the pipe and the water. Thus, the time of flight is then determined using a predetermined search window for the second maximum autocorrelation group from the calculated value of the auto-correlation.

However, when the signals become unstable or when the signals are overlapping it is hard to set a searching window for the autocorrelation in order to find the maximum value and the time-of-fight. One may lose the fidelity of the measurement under this circumstance. For this purpose, different approaches were introduced to characterize time-of-flight by an envelope extraction based on the Hilbert transform technique.

Hilbert Transform Method

The Hilbert transform was originally developed to solve integral equations. The Hilbert transform yields another time series that has been phase shifted by 90° via its integral definition. Recently, the Hilbert transform technique has become widely used for the TOF estimation by using the envelope extraction method. The Hilbert transform has been applied to obtain an analytical signal (a complex envelope) from a real signal to determine instantaneous frequency and envelop estimation [Boashash et al., 1992, Chen et al., 2005, Oruklu et al., 2009]. The analytical signal Z(t) of the echo s(t) is defined in Eq. 2, and the envelope of the analytical signal can be obtained with the magnitude of the signal Z(t).

$$Z(t) = s(t) + jH[s(t)] = a(t)e^{-j\phi(t)} \quad (2)$$

where a(t) is the envelop, $\phi(t)$ is phase, $j=\sqrt{-1}$, and H[s(t)] is Hilbert transform of s(t), defined as the Cauchy principal value of the integral:

$$H[s(t)] = P.V. \int_{-\infty}^{\infty} \frac{s(\tau)}{\pi(t-\tau)} d\tau \quad (3)$$

As an alternative approach, Hilbert transform based signal processing has been developed to determine the time-of-fight. It should be noted that the echoes generally interfere with the noise, which causes the distortion of the frequency spectrum. The signal can to be filtered to overcome this problem. The effect of a high-pass filter is demonstrated in FIG. 25A through FIG. 25D, where the received and the filtered signals with their short time Fourier Transforms (STFT) are presented. It can be seen from the figures that the noise in the reconstructed signal has been greatly reduced and the echoes are clearly visible due to a high-pass filter.

One method to determine the time-of-fight values from the Hilbert envelop is to find the maximum peak and threshold time of the first echo from the pipe wall, which are defined as $T_0$ and $T_1$, respectively. Then, the time $T_m$ of at the local maximum of the second signal group can be found by searching above the threshold time $T_1$. The time-of-fight can thus be found by the time difference $T_m - T_0$ as shown in FIG. 26.

Shannon Energy Envelope

The normalized average Shannon energy known as the Shannon envelope is a widely used signal processing method for envelope extraction of cardiac sound signals [Liang et al., 1997, Choi et al., 2008, Liu et al., 2012]. The Shannon energy SE(t) and average Shannon energy $E_s(t)$ can be defined as follows:

$$S_E(t) = -x_{norm}^2(t) \log x_{norm}^2(t) \quad (4)$$

$$E_s(t) = \frac{1}{N} \sum_{i=1}^{N} x_{norm}^2(i) \log x_{norm}^2(i) \quad (5)$$

where $x_{norm}(t)$ is a normalized signal and N is the signal length, and $E_s(t)$ is the average Shannon energy for frame t. The normalized average Shannon energy N(t), called as the Shannon envelope, is then calculated by as follows.

$$N(t) = \frac{E_s(t) - M(E_s(t))}{S(E_s(t))} \quad (6)$$

where $S(E_s(t))$ is the standard deviation of $E_s(t)$, $M(E_s(t))$ is the mean value of $E_s(t)$.

Figure 27:
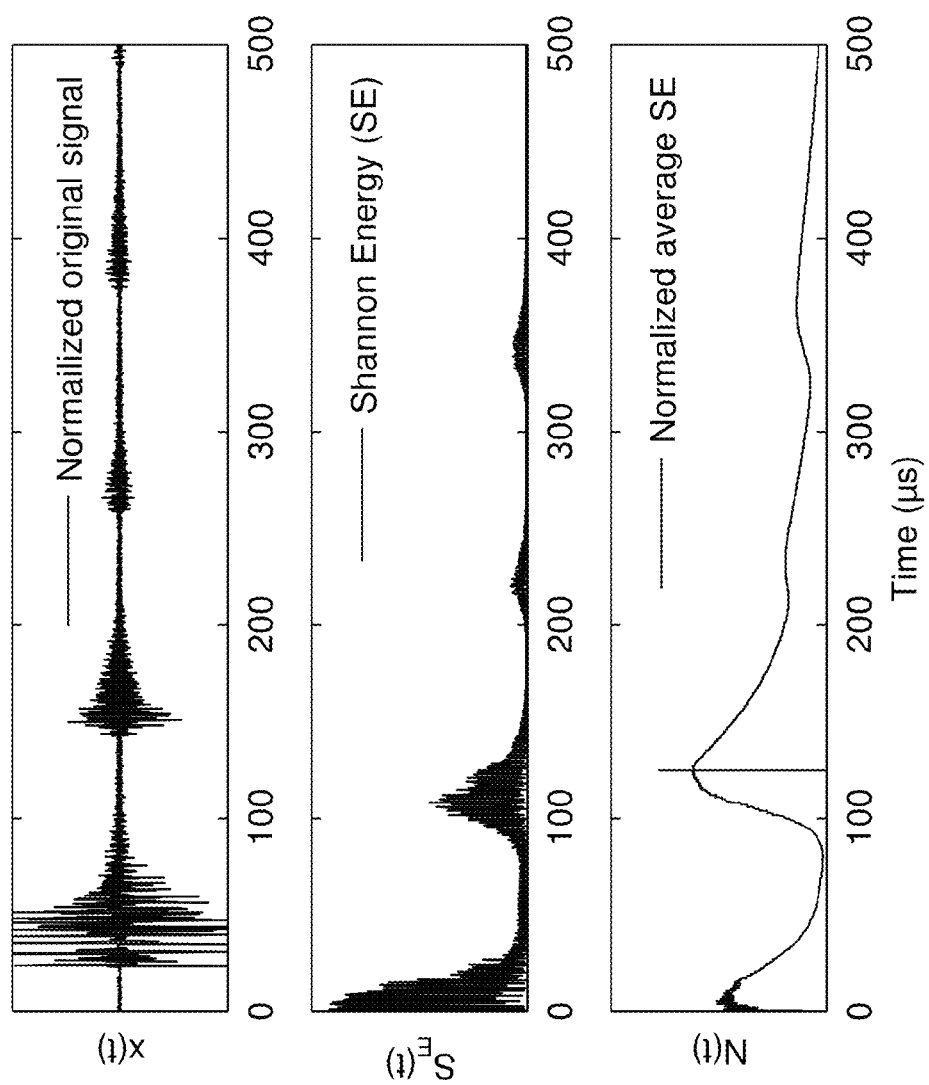
FIG. 27 includes three panels which show as a function of time, from the top to the bottom, respectively, the normalized original signal x(t), the Shannon energy $S_E$(t), and the normalized average Shannon energy N(t).

FIG. 27 includes three panels which show as a function of time, from the top to the bottom, respectively, the normalized original signal x(t), the Shannon energy $S_E(t)$, and the normalized average Shannon energy N(t). FIG. 27 shows an example of Shannon energy and Shannon envelope. Note that this method emphasizes the medium intensity signal, which corresponds to the second maximum value, and attenuates the low and high intensity signals. Thus, the time-of-flight can be obtained by finding the maximum intensity signal.

Figures 28A, 28B:
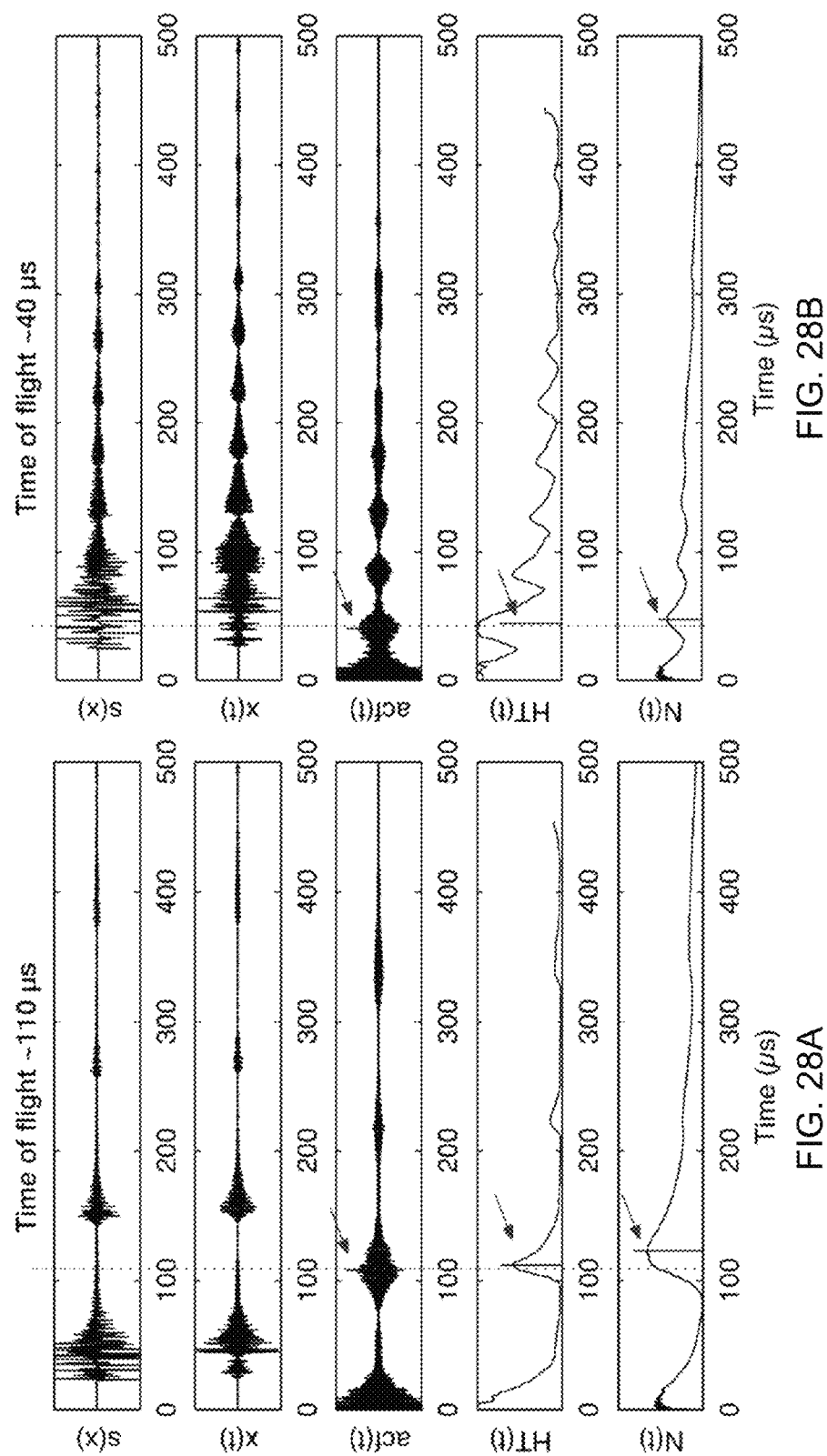
FIG. 28A is a series of graphs showing time signal processing results from received signals in high oil heights. From the top down, they are the original signal s(x), the filtered signal x(t), the autocorrelation of signal acf(t), the Hilbert transform envelope HT(t), and the Shannon energy envelope N(t).
FIG. 28B is a series of graphs showing time signal processing results from received signals in low oil heights. From the top down, they are the original signal s(x), the filtered signal x(t), the autocorrelation of signal acf(t), the Hilbert transform envelope HT(t), and the Shannon energy envelope N(t).

FIG. 28A is a series of graphs showing time signal processing results from received signals in high oil heights. FIG. 28B is a series of graphs showing time signal processing results from received signals in low oil heights. From the top down, they are the original signal s(x), the filtered signal x(t), the autocorrelation of signal acf(t), the Hilbert transform envelope HT(t), and the Shannon energy envelope N(t).

Figures 29A, 29B:
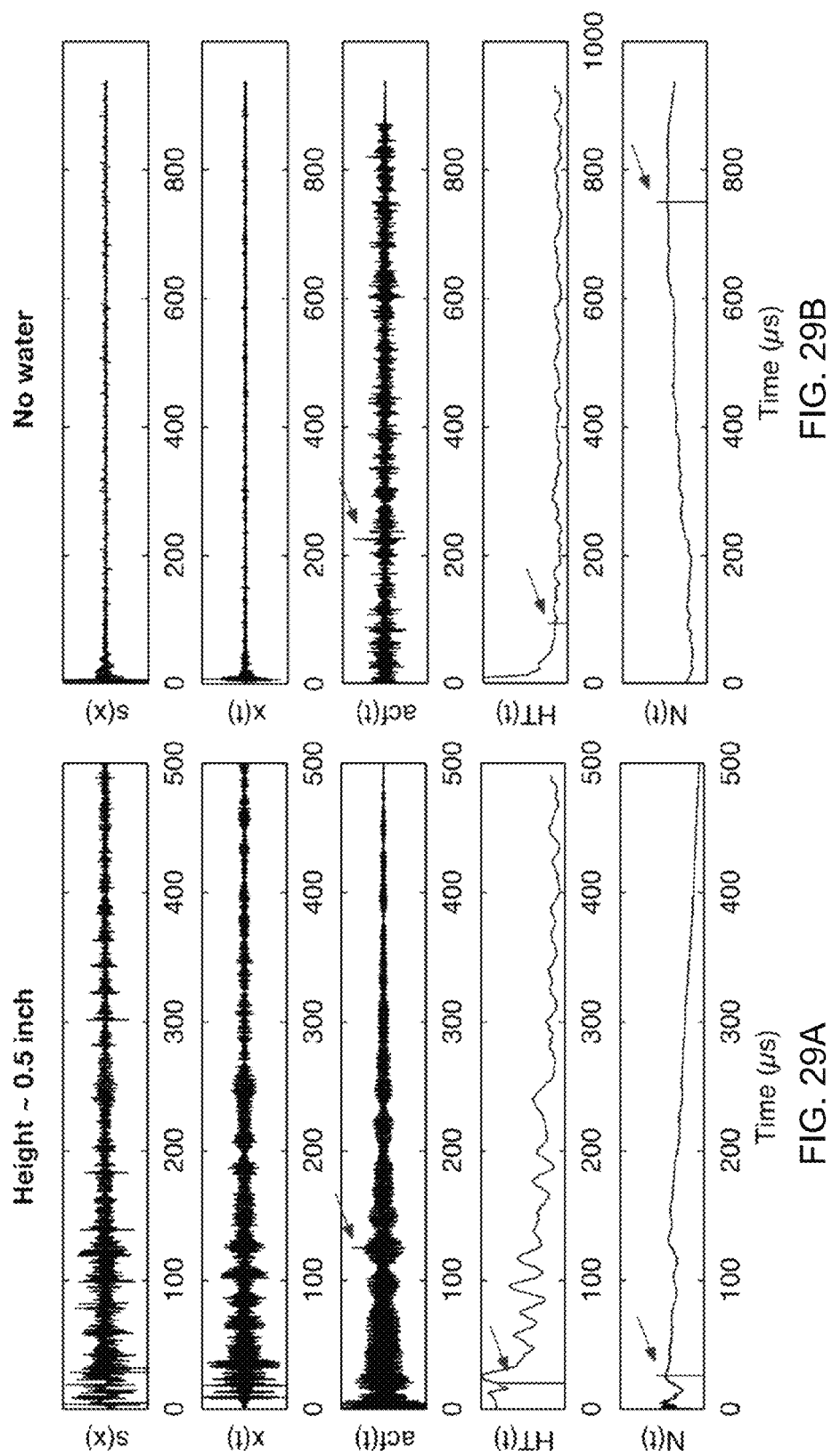
FIG. 29A is a series of graphs showing time signal processing results from received signals in shallow oil. From the top down, they are the original signal s(x), the filtered signal x(t), the autocorrelation of signal acf(t), the Hilbert transform envelope HT(t), and the Shannon energy envelope N(t).
FIG. 29B is a series of graphs showing time signal processing results from received signals in a tube having no water therein. From the top down, they are the original signal s(x), the filtered signal x(t), the autocorrelation of signal acf(t), the Hilbert transform envelope HT(t), and the Shannon energy envelope N(t).

The performance comparison of the methods is shown in FIG. 28A and FIG. 28B for the determination of $T_0$. FIG. 28A shows the original and processed signals when the time-of-flight value was around 110 µs (approximately 7.5 cm of water height). In FIG. 28B the time-of-flight is around 40 µs, corresponding to 2.5 cm of water height. It can be seen that all processing methods provide a reasonable accuracy for the detection of time-of-flight, which is indicated by the small arrows. However, a drawback of this method is that the time-of-flight value is generally overestimated compared to the values determined by autocorrelation and Hilbert envelop methods. The signal processing results obtained from a case of shallow water that is less than 1 inch are shown in FIG. 29A. The limitation of the signal processing methods for low water height is evident as these methods cannot resolve the overlapping echoes. The problem of the autocorrelation method arises from the fact that the noises in the received signals are not only from the ambient noise (white Gaussian noise). They also result from backscattered periodical ringing from the top and bottom of pipe wall.

The consequence is the values of autocorrelation for the received echoes from pipe wall become higher than those of actual echoes from the water surface, making it difficult to determine the time-of-flight when the target water height becomes lower, as shown in FIG. 29A and FIG. 29B. For the Hilbert envelope approach, due to the overlapping signals from the pipe wall and water surface, it may not be able find the time-of-flight value directly. In the Shannon envelope approach, the envelope was found to be flat arising from the fact that the intensity of the reflected echoes are similar at low water height water height, so the Shannon envelope method attenuates all signals. The results conclude that none of the above methods can be used advantageously for the low water height conditions.

In order to improve the accuracy and expand the range of the ultrasonic water height determination, a hybrid frequency analysis method was developed. This hybrid method is based on the Hilbert transform (HT) with a high-pass filter and followed by the fast Fourier transform (FFT) through an optimized windowing technique.

Figures 30A, 30B:
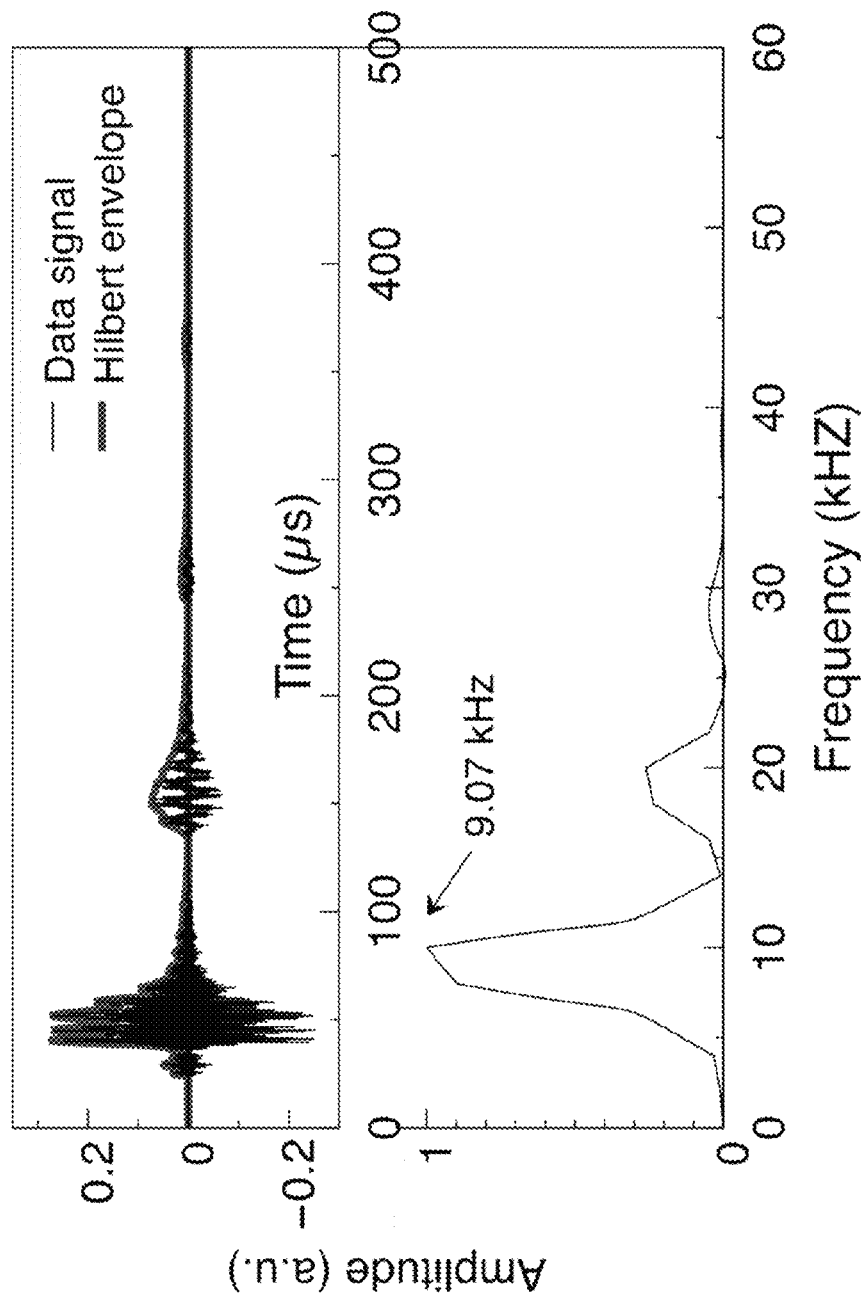
FIG. 30A is a graph showing a reflected signal and its Hilbert envelop as a function of time.
FIG. 30B is a graph showing the fast Fourier transform of a Hilbert envelope as a function of frequency.

An example of the frequency-domain signal by taking the fast Fourier transform (FFT) of a Hilbert envelope is shown in FIG. 30A and FIG. 30B. FIG. 30A is a graph showing a reflected signal and its Hilbert envelop as a function of time.

FIG. 30B is a graph showing the fast Fourier transform of a Hilbert envelope as a function of frequency. It can be seen that the peak frequency occurred at 9.07 kHz, whose inverse is the period of a signal envelope which equals to 110 µs. This value is close to the value physically measured height level. Note that one major issue of the FFT of Hilbert envelope method is that the accuracy of echo frequency strongly depends on the search window length with respect to echo repetition period. Thus, the FFT of Hilbert envelope method was implemented only for a low height of the target, with a narrow search window by cutting the signal in parts and only analyzing a small portion in time. Since the time interval between echoes is short in the low height condition, the analysis of the small part is sufficient to determine the frequency of echo repetition.

Another condition that can arise is monitoring of a steam pipe in the case when there is no condensed (e.g., liquid) water inside the pipe. Since there is no reflection from the water to be detected, the determination from the methods described hereinabove results in wrong time-of-flight values. To further optimize and reduce the errors for the time-of-flight determination, the Hilbert envelop energy algorithm was implemented in the data processing system as a guidance for the presence of water. The energy can be obtained by equation (8) through the integration of the Hilbert envelope over the sampling period T.

$$E^* = \frac{1}{T}\int_0^T HT(t)dt \quad (8)$$

Figures 31A, 31B, 31C:
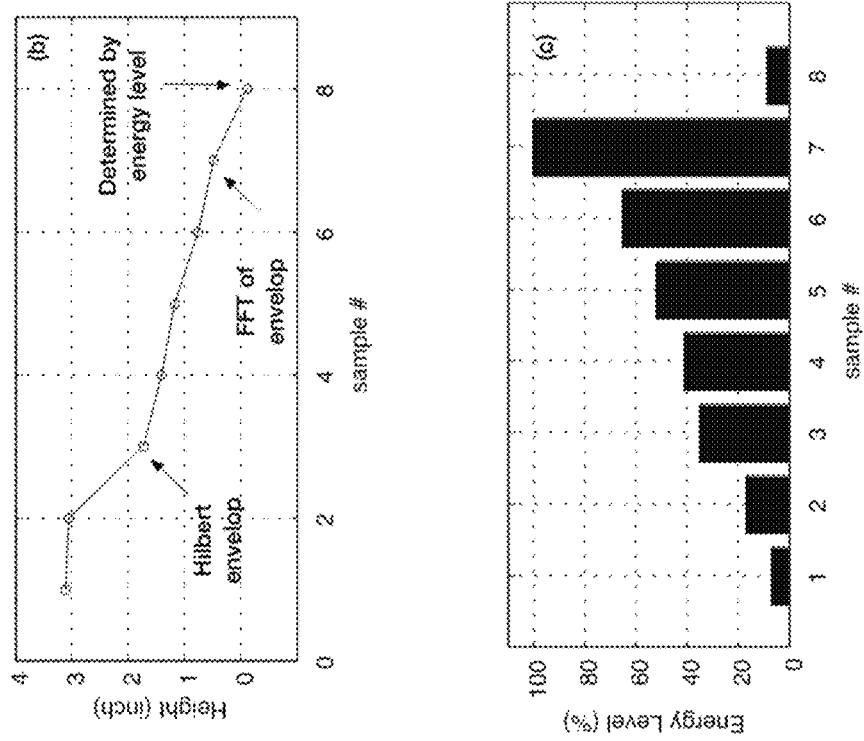
FIG. 31A is a series of graphs showing the received signals from various samples having different water height levels.
FIG. 31B is a graph showing the water height levels determined for several samples.
FIG. 31C is a graph showing the integrated energy level for various samples.

The correlation of energy level with water heights is shown in FIG. 31A, FIG. 31B and FIG. 31C. FIG. 31A is a series of graphs showing the received signals from various samples having different water height levels. FIG. 31B is a graph showing the water height levels determined for several samples. FIG. 31C is a graph showing the integrated energy level for various samples. It can be seen in FIG. 31C that when there is no water or almost no reflections the energy becomes a very low value. Thus, the coherence between the energy level of the echoes and the obtained time-of-flight can be used to verify the time-of-flight value determined to ensure that the measured water height is correct.

Determination of the Cut-Off Frequency of the Hilbert Envelope

Since the ultrasonic waves will also travel between the pipe walls, they will generate high frequency reflection signals in the Hilbert envelope. These reflection signals usually generate many local peaks and valleys and make the determination of water height difficult. Therefore, these signals preferably should be removed. An effective approach was found through the use of a moving average or a low pass filtering process.

Moving Average

A moving average is used to smooth the high frequency contains of the Hilbert envelope. The method can filter out some high frequency noise through the moving average process. However, it is hard to select number of samples for the averaging without the knowing the characters of the signal. Also, over or under averaging may cause the results less useful.

Low Pass Filter Using the Reflection Frequency as the Cut-Off Frequency

Since the ringing of the envelope is caused by the reflection signals between the wall, the reflection frequency $f_{ref}=1/T_{ref}$ is used for the cut-off frequency for the low pass filter, where the reflection period $T_{ref}$ of reflection can be obtained from the round trip time of the ultrasonic wave propagating between the pipe walls. It should be noted that for practical applications the reflection frequency of the signal is usually much lower than the sampling frequency, thus the oscillation due to the sampling can also be removed through this filtering.

Figure 32A:
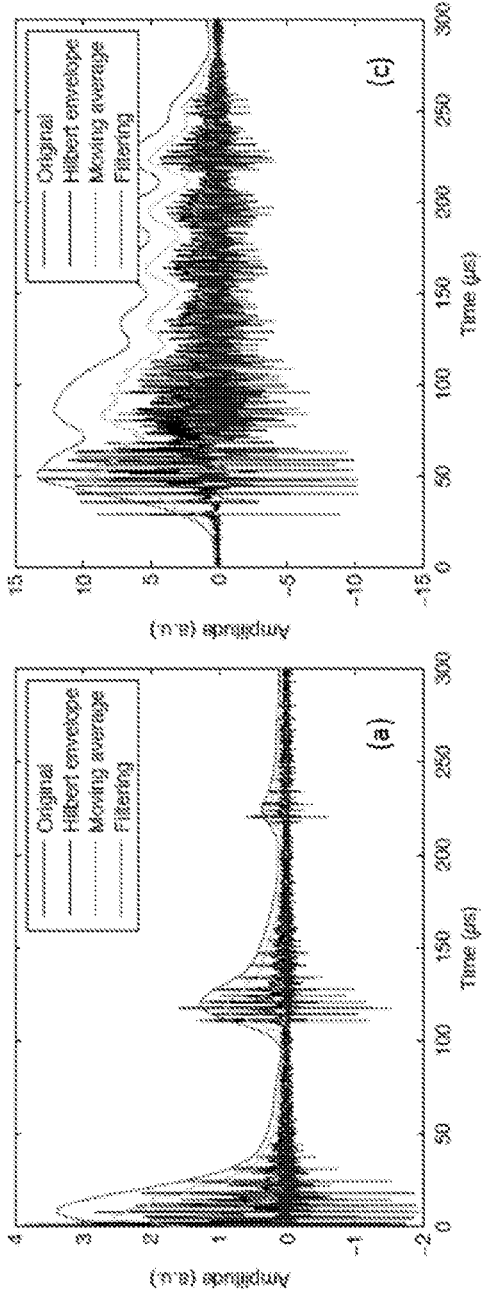
FIG. 32A through FIG. 32D are graphs that show the moving average and the filtered results of the Hilbert envelope for samples in which the water heights decreased from that in FIG. 32A to that in FIG. 32D in sequence.
Figure 32B:
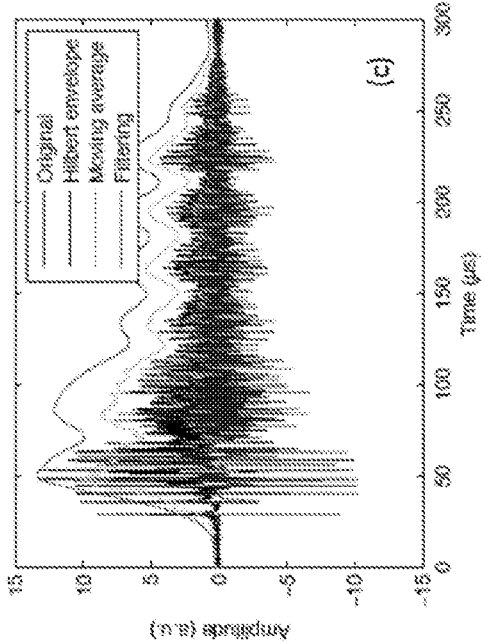
Figure 32C:
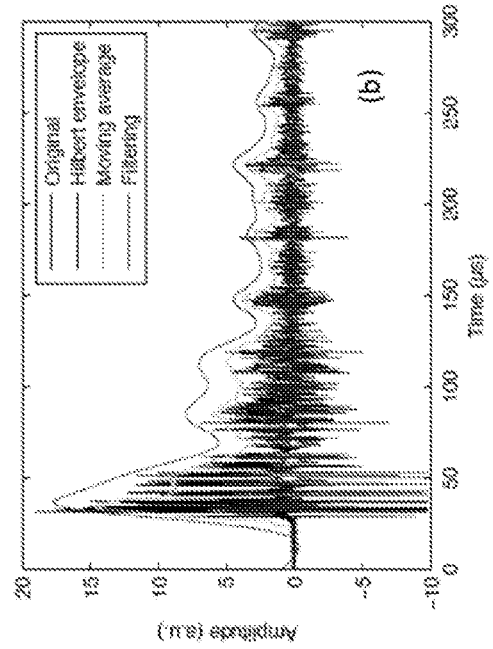
Figure 32D:

FIG. 32A through FIG. 32D are graphs that show the moving average and the filtered results of the Hilbert envelope for samples in which the water heights decreased from that in FIG. 32A to that in FIG. 32D in sequence. It can be seen that the local peaks of the filtered envelope are significant and can be used to identify the time-of-fight of the reflected signal groups even with the overlap of original signals.

Hilbert-Huang Transformation Method

Figure 33:
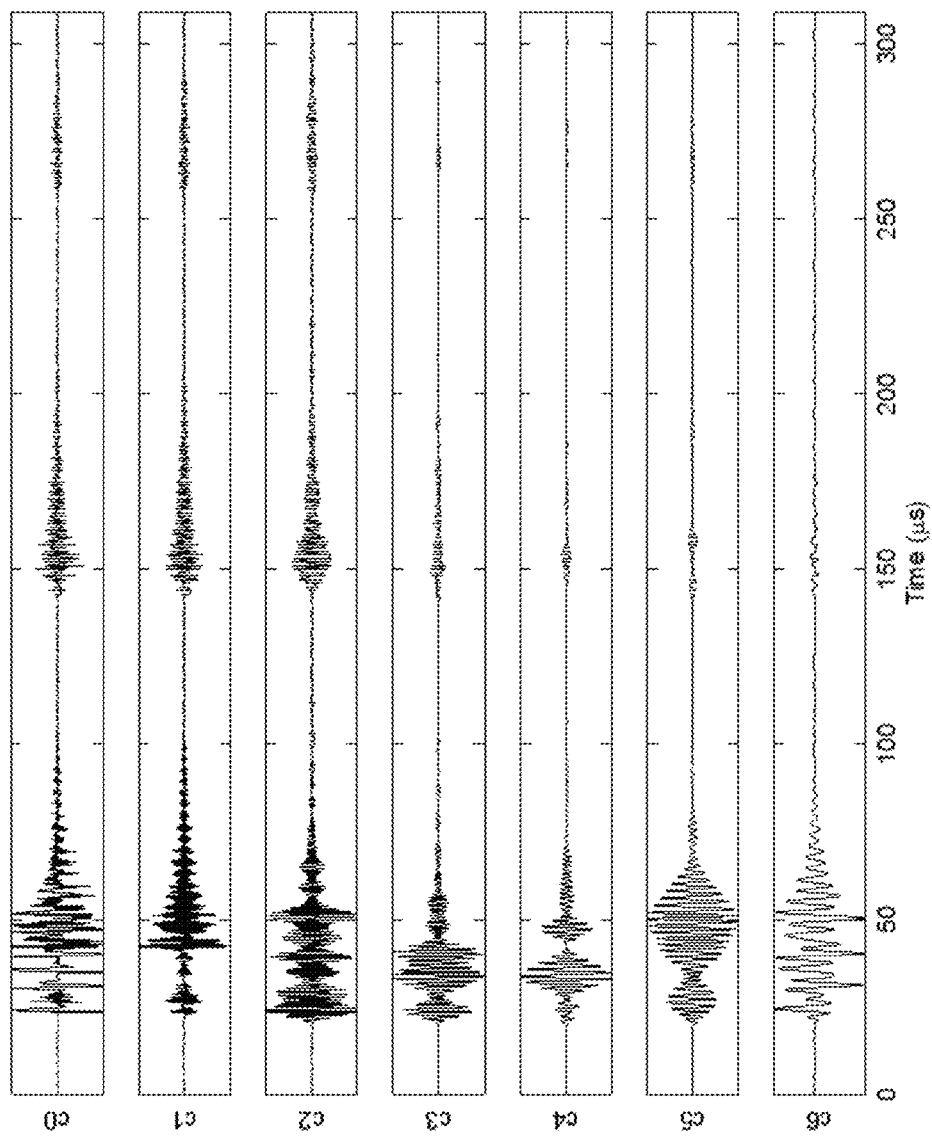
FIG. 33 is a series of graphs of pulse-echo signals using the Empirical mode decomposition (EMD) of the Hilbert-Huang Transformation into a set of band-limited functions (Intrinsic Mode Functions, IMFs) for IMFs c0-c6.

The methods mentioned hereinabove are based on the decomposition of the signals through a high/low-pass or band limit filters, or break the signals into harmonic components through the phase shift, or time to frequency domain transformations such as Hilbert or Fourier Transforms. All these methods are based on the assumption that the signal is stationary. However, when a disturbance happens in the operation of the steam pipe, the signal is usually not stationary and not band limited. Therefore, a method using Empirical Mode Decomposition (EMD) was examined [Huang et al. 1998]. The method uses a sifting process that decomposes a wide class of signals into a set of band-limited functions (Intrinsic Mode Functions, or IMFs). It has been shown that the method is viable to extract instantaneous information from the signal. A result of the pulse-echo signals using the IMF decomposition is shown in FIG. 33. FIG. 33 shows a series pulse-echo signals decomposed into a set of band-limited functions for IMFs c0-c6. In the figure, it can be see the each mode of the IMFs has unique constituents and this can be used for the identification of the disturbances caused by turbulence flow, bubbles, cavitation, shock and vibrations or shallow water conditions in a harsh environment.

The validity and effectiveness of the different computational systems based on algorithms including autocorrelation function, Hilbert Transform, and Shannon envelope methods were demonstrated by using a general purpose programmable computer operating under instructions recorded on a machine readable medium. Alternative solutions for shallow water or no water were also addressed. They include enhanced signal analysis by the Hilbert-Huang Transformation. This method provides a viable tool for the monitoring of the water level inside a pipe or other forms of containers under irregular conditions including turbulent flow, bubble generation, cavitation, shock and vibrations or shallow water conditions.

Computer-Based System and Method

Figure 34:
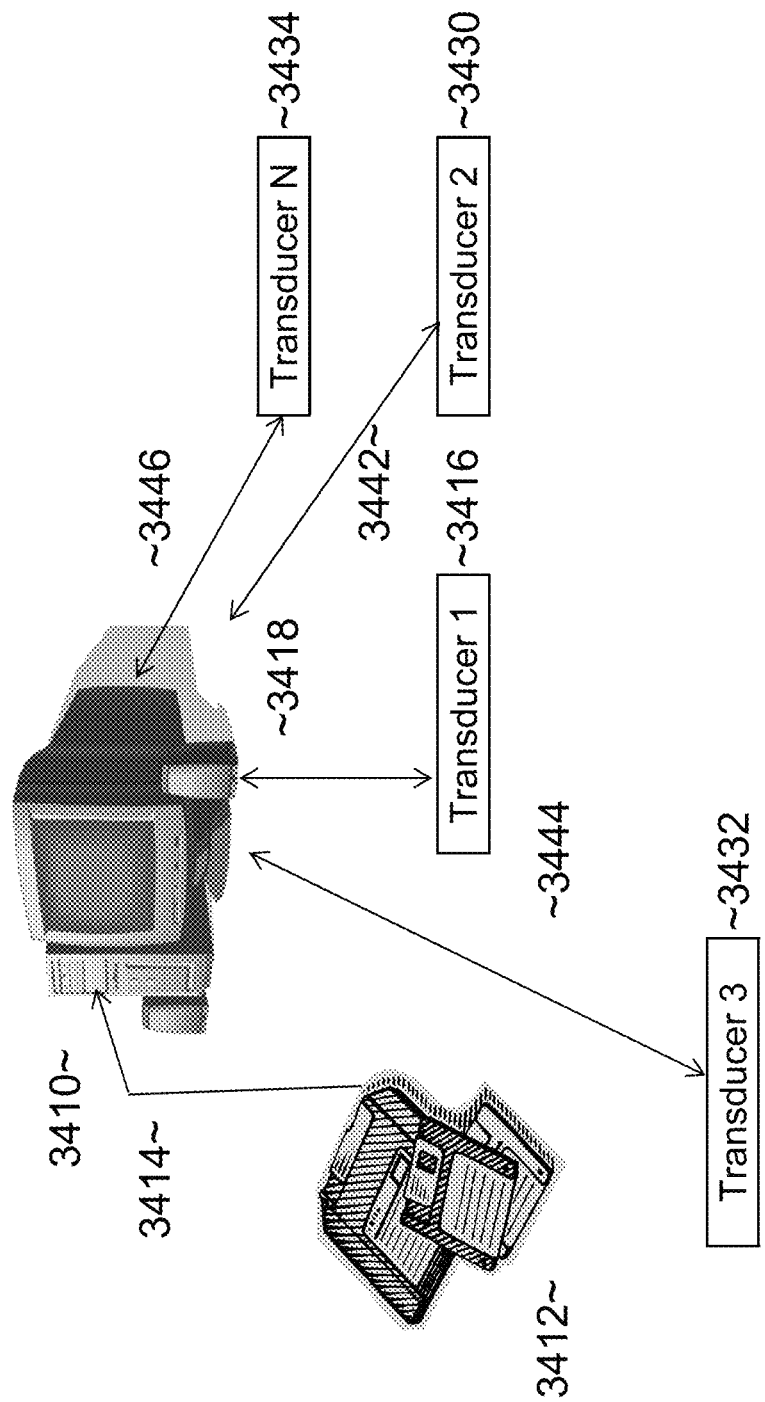
FIG. 34 is a diagram illustrating a general purpose programmable computer-based system that uses the computer code recorded on a machine readable medium to perform the measurements described.

FIG. 34 is a diagram illustrating a general purpose programmable computer-based system that uses the computer code recorded on a machine readable medium to perform the measurements described. As illustrated in FIG. 34, in one embodiment the controller is a computer-based controller 3410, such as a general purpose programmable computer that can be programmed with instructions recorded in a non-volatile manner on a machine-readable medium 3412 such as a magnetic disk. The instructions can be communicated from the machine-readable medium 3412 to the computer-based controller 3410, for example as illustrated by arrow 3414, which can denote that the machine-readable medium 3412 is physically connected to the computer-based controller 3410, or is in electronic communication with the computer-based controller 3410.

When operating on the computer-based controller 3410, the instructions recorded in non-volatile fashion on the machine-readable medium 3412 define methods of operating a plurality of measurement devices (e.g., ultrasonic transducers that can emit an ultrasonic wave and that can receive a reflected wave) 3416, 3430, 3432, 3434. In general, at least one or more measurement devices 3412, 3430, 3432, and 3434 are provided. Measurement device 3416 is in bi-directional communication with controller 3410 as designated by bi-directional arrow 3418. Measurement devices 3430, 3432, 3434 are each in communication with the computer-based controller 3410, as indicated by arrows 3442, 3444 and 3446, respectively. Communication between the computer-based controller 3410 and any of measurement devices 3416, 3430, 3432, 3434 can be performed using any convenient analog or digital protocol, for example any of the IEEE 802 protocols, the International Telecommunications Union (ITU) H.323 protocol, or the Integrated Services Digital Network (ISDN) protocol. The bi-directional communication can be by way of a wired electrical connection, a wireless connection, a fiber optic connection, or any other conventional communication connection. The physical distance between controller 3410 and any of measurement devices 3416, 3430, 3432, 3434 can be any convenient distance.

The computer-based controller 3410 can receive instructions or commands from a user, who can issue such instructions or commands using a device such as a keyboard, a mouse, a touchscreen or any convenient human interface device that communicates with the computer-based controller 3410.

The user can be situated proximate to the computer-based controller 3410, or can be remote from the computer-based controller 3410 and connected to the computer-based controller 3410 using a packet-based communication system such as the Internet.

The computer-based controller 3410 can include a display. If a user is proximate to the computer-based controller 3410, the display can be used to show the user the progress of the communications that are taking place. If the user is remote from the computer-based controller 3410, the information to be displayed can be communicated to a display proximate to the user's location. In particular, either display can be configured to display to the user information indicative of the communications that are taking place.

In order to effectuate communication, each measurement device can include a local processor, such as a microprocessor or a microcontroller, a local memory such as a semiconductor memory, and a local power supply, such as a battery. Each measurement device can be assigned a unique identification, such as a unique alphanumeric string. Alternatively, each transducer can use a unique operating frequency as an identifier. Communication can be carried out according to an agreed protocol.

Figure 35:
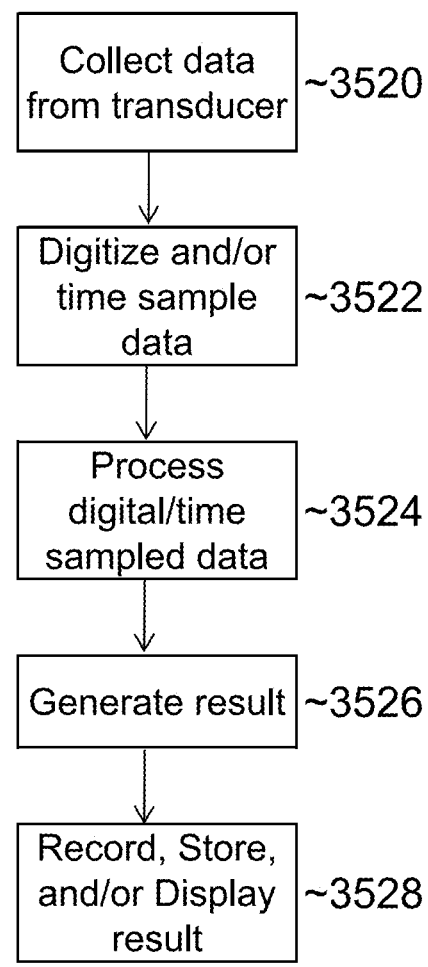
FIG. 35 is a schematic flow diagram of a measurement process that includes data collection and analysis.

FIG. 35 is a schematic flow diagram of a measurement process that includes data collection and analysis. As illustrated in FIG. 35, at step 3520 a command is issued by a controller, such as the computer-based controller 3410. The command can be in response to a directive from a user, or it can be issued based on an instruction in a set of instructions recorded on machine-readable medium 3412. The command directs a measurement device to collect data and/or to report data already collected to the computer-based controller 3410. At step 3522 the data is digitized and/or time sampled as necessary. At step 3524 the computer-based controller 3410 processes the digital/time sampled data. At step 3526 the computer-based controller 3410 generates a result, such as the depth of water at the location of the transducer that provided the data. At step 3528 the computer-based controller 3410 records, and/or stores, and/or displays the result.

DEFINITIONS

Unless otherwise explicitly recited herein, any reference to an electronic signal or an electromagnetic signal (or their equivalents) is to be understood as referring to a non-volatile electronic signal or a non-volatile electromagnetic signal.

Recording the results from an operation or data acquisition, such as for example, recording results at a particular frequency or wavelength is understood to mean and is defined herein as writing output data in a non-transitory manner to a storage element, to a machine-readable storage medium, or to a storage device. Non-transitory machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. Unless otherwise explicitly recited, any reference herein to "record" or "recording" is understood to refer to a non-transitory record or a non-transitory recording.

As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes. Recording image data for later use (e.g., writing an image to memory or to digital memory) can be performed to enable the use of the recorded information as output, as data for display to a user, or as data to be made available for later use. Such digital memory elements or chips can be standalone memory devices, or can be incorporated within a device of interest. "Writing output data" or "writing an image to memory" is defined herein as including writing transformed data to registers within a microcomputer.

"Microcomputer" is defined herein as synonymous with microprocessor, microcontroller, and digital signal processor ("DSP"). It is understood that memory used by the microcomputer, including for example instructions for data processing coded as "firmware" can reside in memory physically inside of a microcomputer chip or in memory external to the microcomputer or in a combination of internal and external memory. Similarly, analog signals can be digitized by a standalone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. Apparatus having any of the inventive features described herein can operate entirely on one microcomputer or can include more than one microcomputer.

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of Mac OS, or of UNIX, or of Linux. Computational results obtained in the operation of the general purpose computer can be stored for later use, and/or can be displayed to a user. At the very least, each microprocessor-based general purpose computer has registers that store the results of each computational step within the microprocessor, which results are then commonly stored in cache memory for later use.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein, so long as at least some of the implementation is performed in hardware.

Theoretical Discussion

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, or publication identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. A monitoring system for determining the status of a steam pipe, comprising:
    a programmable computer which when operating under control of a set of instructions recorded on a machine readable memory performs the steps of:
        controlling the emission of a probe ultrasonic signal having a frequency in the range of 2.25 Mega Hertz and above from an ultrasonic signal generator into a steam pipe;
        receiving from an ultrasonic signal receiver an electrical signal representative of an ultrasonic response signal which is generated in said steam pipe in response to said probe ultrasonic signal;
        processing said electrical signal by application of one or more of a filter, a moving average, a window, a transformation, a Shannon Energy Envelope and an auto-correlation method to produce a result representing a status of said steam pipe; and
        performing at least one of recording said result, displaying said result, and transmitting said result to another system.

2. The monitoring system for determining the status of a steam pipe of claim 1, wherein said filter is selected from the group consisting of a low pass filter, a high pass filter and a band limit filter.

3. The monitoring system for determining the status of a steam pipe of claim 1, wherein said window is a predetermined searching window.

4. The monitoring system for determining the status of a steam pipe of claim 1, wherein said transformation is selected from the group consisting of a time to frequency domain transformation, Fourier Transform, a Hilbert Transform, and a Hilbert-Huang Transformation.

5. The monitoring system for determining the status of a steam pipe of claim 1, wherein said ultrasonic signal generator and said ultrasonic signal receiver are the same ultrasonic device.

6. The monitoring system for determining the status of a steam pipe of claim 1, wherein said programmable computer which when operating under control of a set of instructions recorded on a machine readable memory performs the additional step of converting said electrical signal from an analog signal to a digital signal.

7. The monitoring system for determining the status of a steam pipe of claim 1, wherein said result representing a status of said steam pipe includes information about liquid water in said stem pipe.

8. The monitoring system for determining the status of a steam pipe of claim 7, wherein said information about liquid water in said steam pipe is indicative of a depth of said liquid water.

9. The monitoring system for determining the status of a steam pipe of claim 7, wherein said information about liquid water in said steam pipe is indicative of at least one of a turbulent flow, of bubble generation, of cavitation, of a shock and of a vibration in said liquid water.

10. The monitoring system for determining the status of a steam pipe of claim 1, wherein said programmable computer is a general purpose programmable computer.

11. A non-transitory machine-readable medium having recorded thereon a set of instructions, said instructions comprising only non-volatile signals, which when operating on a programmable computer causes said programmable computer to perform the steps of:
- controlling the emission of a probe ultrasonic signal having a frequency in the range of 2.25 Mega Hertz and above from an ultrasonic signal generator into a steam pipe;
- receiving from an ultrasonic signal receiver an electrical signal representative of an ultrasonic response signal which is generated in said steam pipe in response to said probe ultrasonic signal;
- processing said electrical signal by application of one or more of a filter, a moving average, a window, a transformation, a Shannon Energy Envelope and an autocorrelation method to produce a result representing a status of said steam pipe; and
- performing at least one of recording said result, displaying said result, and transmitting said result to another system.

12. The non-transitory machine-readable medium having recorded thereon a set of instructions of claim 11, wherein said filter is selected from the group consisting of a low pass filter, a high pass filter and a band limit filter.

13. The non-transitory machine-readable medium having recorded thereon a set of instructions of claim 11, wherein said window is a predetermined searching window.

14. The non-transitory machine-readable medium having recorded thereon a set of instructions of claim 11, wherein said transformation is selected from the group consisting of a time to frequency domain transformation, Fourier Transform, a Hilbert Transform, and a Hilbert-Huang Transformation.

15. The non-transitory machine-readable medium having recorded thereon a set of instructions of claim 11, wherein said ultrasonic signal generator and said ultrasonic signal receiver are the same ultrasonic device.

16. The non-transitory machine-readable medium having recorded thereon a set of instructions of claim 11, wherein said programmable computer is caused to perform the additional step of converting said electrical signal from an analog signal to a digital signal.

17. The non-transitory machine-readable medium having recorded thereon a set of instructions of claim 11, wherein said result representing a status of said steam pipe includes information about liquid water in said stem pipe.

18. The non-transitory machine-readable medium having recorded thereon a set of instructions of claim 17, wherein said information about liquid water in said steam pipe is indicative of a depth of said liquid water.

19. The non-transitory machine-readable medium having recorded thereon a set of instructions of claim 17, wherein said information about liquid water in said steam pipe is indicative of at least one of a turbulent flow, of bubble generation, of cavitation, of a shock and of a vibration in said liquid water.

20. The non-transitory machine-readable medium having recorded thereon a set of instructions of claim 11, wherein said programmable computer is a general purpose programmable computer.

* * * * *